US012570618B2

(12) United States Patent
Shiina et al.

(10) Patent No.: US 12,570,618 B2
(45) Date of Patent: Mar. 10, 2026

(54) COMPOUND, PRODUCTION METHOD THEREFOR, AND PHARMACEUTICAL COMPOSITION

(71) Applicants: TOKYO UNIVERSITY OF SCIENCE FOUNDATION, Tokyo (JP); NATIONAL CANCER CENTER, Tokyo (JP)

(72) Inventors: Isamu Shiina, Tokyo (JP); Motoyuki Shimonaka, Tokyo (JP); Takatsugu Murata, Tokyo (JP); Yuuki Obata, Tokyo (JP); Toshirou Nishida, Tokyo (JP); Koji Okamoto, Tokyo (JP)

(73) Assignees: TOKYO UNIVERSITY OF SCIENCE FOUNDATION, Tokyo (JP); NATIONAL CANCER CENTER, Tokyo (JP)

( * ) Notice: Subject to any disclaimer, the term of this patent is extended or adjusted under 35 U.S.C. 154(b) by 421 days.

(21) Appl. No.: 18/263,513

(22) PCT Filed: Jan. 28, 2022

(86) PCT No.: PCT/JP2022/003317

§ 371 (c)(1),
(2) Date: Jul. 28, 2023

(87) PCT Pub. No.: WO2022/172786

PCT Pub. Date: Aug. 18, 2022

(65) Prior Publication Data

US 2024/0140918 A1 May 2, 2024

(30) Foreign Application Priority Data

Feb. 10, 2021 (JP) ................................ 2021-020207

(51) Int. Cl.
*C07D 263/32* (2006.01)
*C07D 213/56* (2006.01)
*C07D 277/30* (2006.01)

(52) U.S. Cl.
CPC ......... *C07D 263/32* (2013.01); *C07D 213/56* (2013.01); *C07D 277/30* (2013.01)

(58) Field of Classification Search
None
See application file for complete search history.

(56) References Cited

U.S. PATENT DOCUMENTS

2007/0142539 A1 6/2007 Yamada

FOREIGN PATENT DOCUMENTS

| | | | |
|---|---|---|---|
| EP | 1702910 | A1 | 9/2006 |
| KR | 10-2016-0138759 | A | 12/2016 |
| WO | WO 2005/070856 | A1 | 8/2005 |
| WO | WO 2013/151161 | A1 | 10/2013 |

OTHER PUBLICATIONS

Cardoso-Martinez Faviola et al: “Tanzawaic acids isolated from a marine-derived fungus of the genus *Penicillium* with cytotoxic activities”, Organic & Biomolecular Chemistry, vol. 13, No. 26, May 2015, pp. 7248-7256.

Extended European Search Report issued Jul. 4, 2024 in European Patent Application No. 22752615.9 in 8 pages.

Hara, Y. et al., “M-COPA suppresses endolysosomal Kit-Akt oncogenic signalling through inhibiting the secretory pathway in neoplastic mast cells” PLOS ONE, 2017 ; 12(4) : e0175514, 2017.

Obata, Y. et al., “Oncogenic Kit signalling on the Golgi is suppressed by blocking secretory trafficking with M-COPA in gastrointestinal stromal tumours” Cancer Lett., 2018 ; 415(1) : 1-10, 2018.

Obata, Y. et al., “N822K- or V560G-mutated KIT activation preferentially occurs in lipid rafts of the Golgi apparatus in leukemia cells” Cell Commun. Signal., 2019 ; 17(1) : 114, 2019.

Ohashi, Y. et al., “M-COPA, a Golgi Disruptor, Inhibits Cell Surface Expression of MET Protein and Exhibits Antitumor Activity against MET-Addicted Gastric Cancers” Cancer Res., 2016 ; 76(13) : 3895-3903, 2016.

Ohashi, Y. et al., “Targeting the Golgi apparatus to overcome acquired resistance of non-small cell lung cancer cells to EGFR tyrosine kinase inhibitors”, Oncotarget, 2018 ; 9(2) : 1641-1655, 2017.

Shiina, I. et al., “Total Synthesis of AMF-26, an Antitumor Agent for Inhibition of the Golgi System, Targeting ADP -Ribosylation Factor 1” Journal of Medicinal Chemistry, 2013, vol. 56, No. 1, pp. 150-159, ISSN: 0022-2623 , entire text, 2013.

(Continued)

*Primary Examiner* — Valerie Rodriguez-Garcia
(74) *Attorney, Agent, or Firm* — KNOBBE, MARTENS, OLSON & BEAR, LLP

(57) ABSTRACT

A compound represented by formula (1) below, useful for treating cancer. In the formula, $R^1$ and $R^3$-$R^8$ each independently represents a hydrogen atom or an alkyl group, $R^2$ represents a hydrogen atom or a group represented by —$OR^a$, $R^9$ represents a group represented by —$C(O)NR^eR^f$, $R^a$, $R^e$, and $R^f$ each independently represents a hydrogen atom, an arylalkyl group that may have a substituent, or a heteroarylalkyl group. A production method that enables the compound to be produced with high efficiency, and a pharmaceutical composition containing the compound as an active ingredient (1)

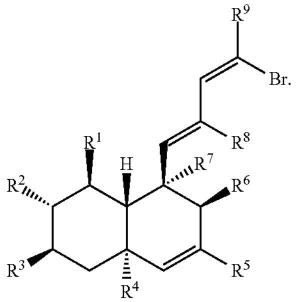

7 Claims, 3 Drawing Sheets

(56) References Cited

OTHER PUBLICATIONS

Zhang, X. et al., "Synthesis of 2',3'-Dideoxy-2'-trifluoromethylnucleosides from α-Trifluoromethyl-α, β-unsaturated Ester" Journal of Organic Chemistry, 2000, vol. 65, No. 21, pp. 7075-7082, ISSN. 0022-3263 , entire text, 2000.
Zhang, X. et al., "A new route to α-trifluoromethyl-α, β-unsaturated esters" Tetrahedron Letters, 2000, vol. 41, No. 16, pp. 2953-2955, ISSN: 0040-4039 entire text, 2000.

COMPOUND, PRODUCTION METHOD THEREFOR, AND PHARMACEUTICAL COMPOSITION

CROSS-REFERENCE TO RELATED APPLICATIONS

This application is the U.S. National Phase under 35 U.S.C. § 371 of International Application PCT/JP2022/003317, filed Jan. 28, 2022, designating the U.S., and published in Japanese as WO 2022/172786 on Aug. 18, 2022 which claims priority to Japanese Patent Application No. 2021-020207 filed Feb. 10, 2021.

TECHNICAL FIELD

The present invention relates to a novel compound, a production method therefor, and a pharmaceutical composition.

BACKGROUND ART

M-COPA (2-methylcoprophilinamide [AMF-26]) is a compound having a structure shown below, and is known to exhibit anticancer action.

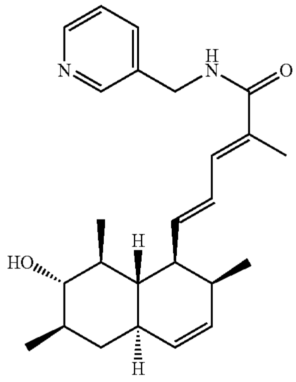

M-COPA

M-COPA has been recently revealed to exhibit anticancer action by inhibiting, for example, the translocation of receptor tyrosine kinases (such as MET, EGFR, KIT) to a Golgi apparatus or a cellular membrane via suppression of transport of them between the endoplasmic reticulum and Golgi apparatus (e.g., see Non-Patent Documents 1 to 5), and is expected to be promising for use as a next-generation molecular target anticancer agent targeting Golgi apparatus.

M-COPA was conventionally synthesized from a natural compound derived from the ascomycete Trichoderma as a raw material, and the mass synthesis thereof was difficult. In view of this, Patent Document 1 has proposed a method for synthesizing M-COPA and an analog thereof without use of a natural product.

An excerpt from the description of the method for synthesizing M-COPA in Patent Document 1 is as follows. First, compound a is cyclized through intramolecular Diels-Alder reaction and reduced to give compound b, and compound b is then oxidized to give compound c. Subsequently, compound c is subjected to Horner-Wadsworth-Emmons reaction to give compound d, which is then hydrolyzed to give compound e. Thereafter, compound e is amidated by reacting with 3-aminomethylpyridine, and then deprotected to give M-COPA.

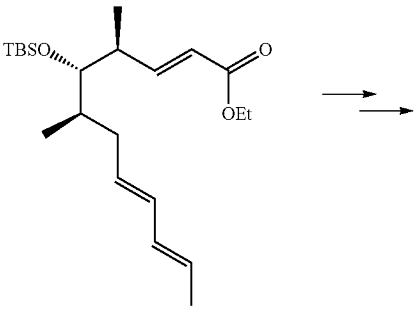

a

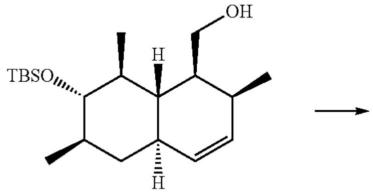

b

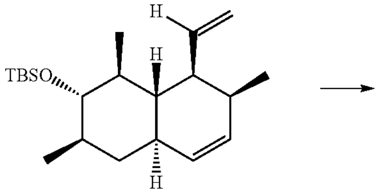

c

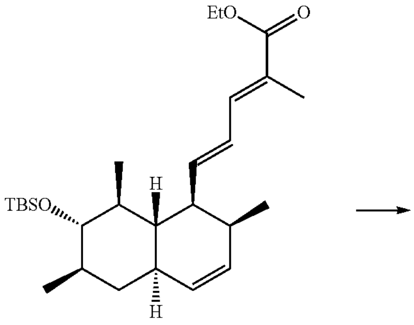

d

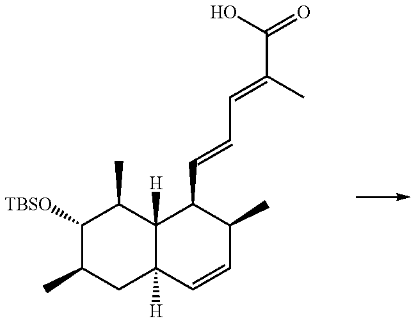

e

-continued

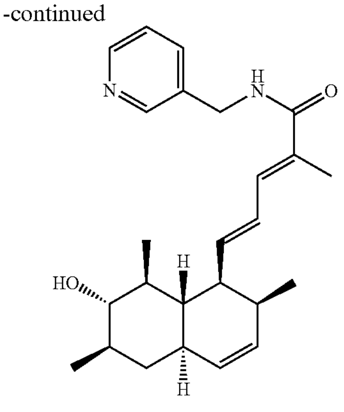

M-COPA

Patent Document 1: PCT International Publication No. WO 2013/151161

Non-Patent Document 1: Y. Ohashi et al., Cancer Res., 2016; 76 (13): pp. 3895-3903

Non-Patent Document 2: Y. Hara et al., PLOS ONE, 2017; 12 (4): e0175514

Non-Patent Document 3: Y. Ohashi et al., Oncotarget, 2018; 9 (2): pp. 1641-1655

Non-Patent Document 4: Y. Obata et al., Cancer Lett., 2018; 415 (1): pp. 1-10

Non-Patent Document 5: Y. Obata et al., Cell Commun. Signal., 2019; 17 (1): 114

DISCLOSURE OF THE INVENTION

Problems to be Solved by the Invention

As described above, while M-COPA is expected to be promising for use as a next-generation molecular target anticancer agent, development of new analogs derived from M-COPA as a lead compound is also desired.

In the synthesis method described in Patent Document 1, a bulky group is present at the a position of the aldehyde group possessed by compound c, a synthesis intermediate, and a hydrogen atom at the a position is then inverted to cause epimerization, which results in a problem of lowered yields of a target substance. Accordingly, development of a new synthesis method is also desired.

The present invention has been proposed in view of such circumstances, and an object of the present invention is to provide: a novel compound useful for cancer treatment or the like; a production method that enables the novel compound to be produced with high efficiency; and a pharmaceutical composition containing the novel compound as an active ingredient.

Means for Solving the Problems

Specific means for solving the problems include the following aspects.

<1> A compound represented by formula (1) below:

(1)

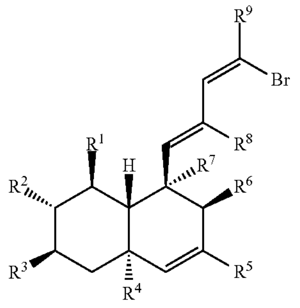

wherein $R^1$ and $R^3$ to each independently represent a hydrogen atom or an alkyl group; $R^2$ represents a hydrogen atom, or a group represented by —$OR^a$ or —$NR^bR^c$; $R^9$ represents a group represented by —$CH_2OR^d$, —$C(O)OR^d$, —$C(O)R^d$, —$CH_2NR^eR^f$, or —$C(O)NR^eR^f$; and $R^a$ to $R^f$ each independently represent a hydrogen atom, an alkyl group, an aryl group optionally having a substituent, a heteroaryl group optionally having a substituent, an arylalkyl group optionally having a substituent, or a heteroarylalkyl group optionally having a substituent.

<2> The compound according to aspect <1>, wherein, in formula (1), $R^1$ and $R^5$ are each independently an alkyl group, $R^2$ is a hydroxy group, $R^4$, $R^5$, $R^7$, and $R^8$ are each a hydrogen atom, $R^9$ is a group represented by —$C(O)OR^d$ or —$C(O)NR^eR^f$, $R^d$ is an arylalkyl group or a heteroarylalkyl group, $R^e$ is a hydrogen atom, and $R^f$ is an arylalkyl group or a heteroarylalkyl group.

<3> A synthesis intermediate of the compound according to aspect <1> or <2>, wherein the synthesis intermediate is represented by formula (3) below:

(3)

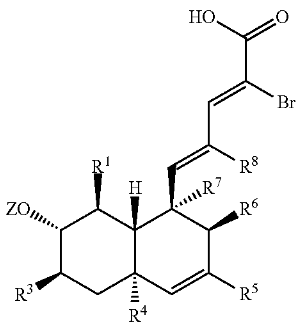

wherein $R^1$ and $R^3$ to $R^8$ each independently represent a hydrogen atom or an alkyl group; and Z represents a protecting group for a hydroxy group.

<4> A production method for producing a compound represented by formula (1) below:

(1)

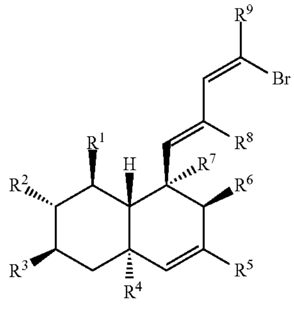

wherein $R^1$ and $R^3$ to $R^8$ each independently represent a hydrogen atom or an alkyl group; $R^2$ represents a hydrogen atom, or a group represented by $—OR^a$ or $—NR^bR^c$; $R^9$ represents a group represented by $—CH_2OR^d$, $—C(O)OR^d$, $—C(O)R^d$, $—CH_2NR^eR^f$, or $—C(O)NR^eR^f$; and $R^a$ to $R^f$ each independently represent a hydrogen atom, an alkyl group, an aryl group optionally having a substituent, a heteroaryl group optionally having a substituent, an arylalkyl group optionally having a substituent, or a heteroarylalkyl group optionally having a substituent, the production method including producing the compound represented by formula (1) from a compound represented by formula (3) below:

(3)

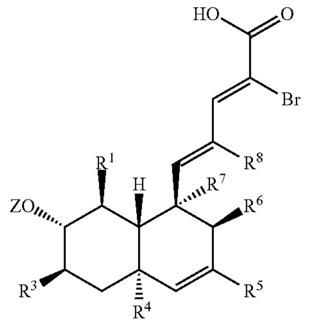

wherein $R^1$ and $R^3$ to $R^8$ are as described above; and Z represents a protecting group for a hydroxy group.

<5> The production method according to <4>, including producing the compound represented by formula (3) by subjecting a compound represented by formula (6) below and a compound represented by formula (5) below to Horner-Wadsworth-Emmons reaction followed by hydrolysis:

(6)

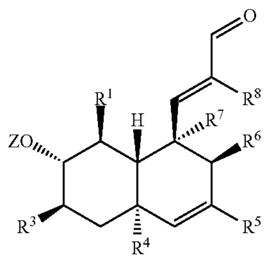

wherein $R^1$, $R^3$ to $R^8$, and Z are as described above, (5)

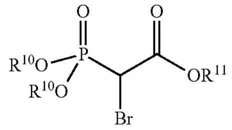

wherein $R^{10}$ and $R^{11}$ each independently represent an alkyl group.

<6> The production method according to aspect <5>, including producing the compound represented by formula (6) by cyclizing a compound represented by formula (7) below through intramolecular Diels-Alder reaction:

(7)

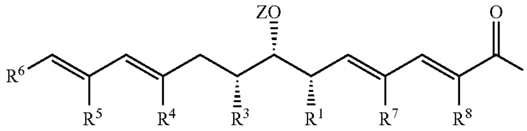

wherein $R^1$, $R^3$ to $R^8$, and Z are as described above.

<7> A pharmaceutical composition containing the compound according to aspect <1> or <2> and a pharmaceutically acceptable carrier.

Effects of the Invention

The present invention can provide: a novel compound useful for cancer treatment or the like; a production method that enables the novel compound to be produced with high efficiency; and a pharmaceutical composition containing the novel compound as an active ingredient.

PREFERRED MODE FOR CARRYING OUT THE INVENTION

<Compound Represented by Formula (1)>

Figure 1:
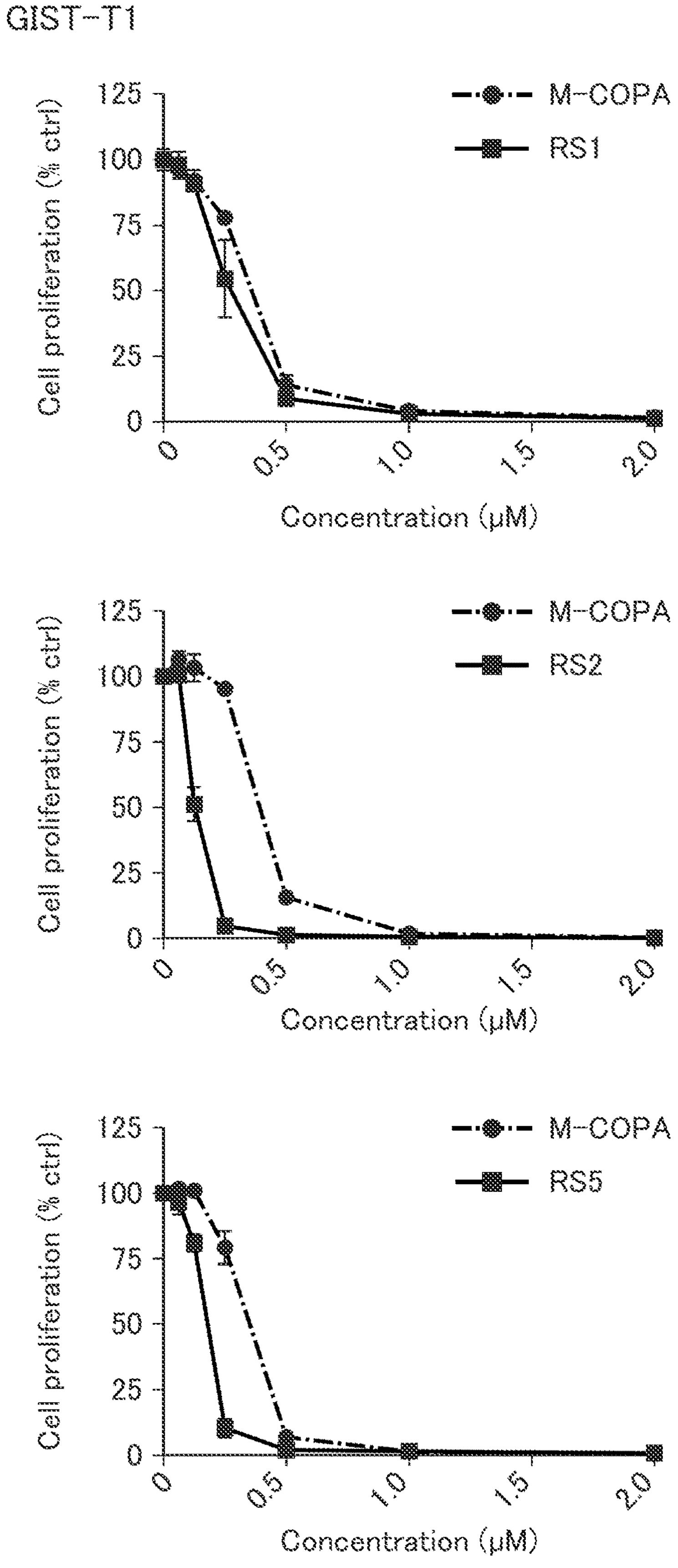
FIG. 1 is graphs showing cell culture curves obtained in culturing GIST-T1 cells in the presence of a compound (RS1, RS2, RS5, or M-COPA) at different concentrations.

The compound according to the present embodiment is represented by formula (1) below.

(1)

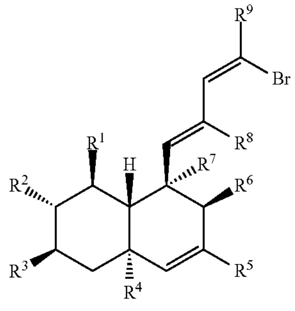

In formula (1), $R^1$ and $R^3$ to $R^8$ each independently represent a hydrogen atom or an alkyl group. $R^2$ represents a hydrogen atom, or a group represented by —$OR^a$ or —$NR^bR^c$. $R^9$ represents a group represented by —$CH_2OR^d$, —$C(O)OR^d$, —$C(O)R^d$, —$CH_2NR^eR^f$, or —$C(O)NR^eR^f$. $R^a$ to $R^f$ each independently represent a hydrogen atom, an alkyl group, an aryl group optionally having a substituent, a heteroaryl group optionally having a substituent, an arylalkyl group optionally having a substituent, or a heteroarylalkyl group optionally having a substituent.

The alkyl group for $R^1$ and $R^3$ to $R^8$ is preferably an alkyl group having 1 to 20 carbon atoms, and more preferably an alkyl group having one to six carbon atoms. The alkyl group may be linear, branched, or cyclic. Specific examples of the alkyl group include a methyl group, an ethyl group, a propyl group, an isopropyl group, a butyl group, a sec-butyl group, an isobutyl group, a tert-butyl group, a pentyl group, an isopentyl group, a cyclopentyl group, a hexyl group, and a cyclohexyl group.

$R^1$ and $R^6$ are preferably each independently an alkyl group (in particular, an alkyl group having one to six carbon atoms), $R^3$ is preferably a hydrogen atom or an alkyl group (in particular, an alkyl group having one to six carbon atoms), and $R^4$, $R^5$, $R^7$, and $R^8$ are preferably each a hydrogen atom.

The alkyl group for $R^a$ to $R^f$ is preferably an alkyl group having 1 to 20 carbon atoms, and more preferably an alkyl group having one to six carbon atoms. The alkyl group may be linear, branched, or cyclic. Specific examples of the alkyl group include a methyl group, an ethyl group, a propyl group, an isopropyl group, a butyl group, a sec-butyl group, an isobutyl group, a tert-butyl group, a pentyl group, an isopentyl group, a cyclopentyl group, a hexyl group, and a cyclohexyl group.

The aryl group for $R^a$ to $R^f$ is preferably a monocyclic or polycyclic aromatic hydrocarbon group having 6 to 20 carbon atoms, and more preferably a monocyclic or polycyclic aromatic hydrocarbon group having 6 to 12 carbon atoms. Specific examples of the aryl group include a phenyl group, a naphthyl group, an anthryl group, a phenanthryl group, and a pyrenyl group.

The heteroaryl group for $R^a$ to $R^f$ is preferably a monocyclic or polycyclic aromatic heterocyclic group having two to nine ring-constituting carbon atoms, and more preferably a monocyclic aromatic heterocyclic group having three to five ring-constituting carbon atoms, each group containing one to four heteroatoms selected from an oxygen atom, a sulfur atom, and a nitrogen atom. Specific examples of the heteroaryl group include a pyrrolyl group, a pyridyl group, an imidazolyl group, a pyrazolyl group, a pyrazinyl group, a pyridazinyl group, a pyrimidinyl group, a triazolyl group, a tetrazolyl group, a furanyl group, a thienyl group, an oxazolyl group, an isoxazolyl group, an oxadiazolyl group, a thiazolyl group, an isothiazolyl group, a thiadiazolyl group, an indolyl group, an isoindolyl group, a benzimidazolyl group, an indazolyl group, a benzothiazolyl group, a tetrahydroquinolyl group, a quinolyl group, a tetrahydroisoquinolyl group, an isoquinolyl group, a quinolidinyl group, a cinnolinyl group, a phthalazinyl group, a quinazolinyl group, a quinoxalinyl group, a naphthyridinyl group, a pyrrolopyridyl group, an imidazopyridyl group, a pyrazolopyridyl group, a pyridopyrazyl group, a purinyl group, a pteridinyl group, a benzofuranyl group, an isobenzofuranyl group, a benzothienyl group, a benzoxazolyl group, a benzisoxazolyl group, a benzoxadiazolyl group, a benzothiazolyl group, a benzoisothiazolyl group, a benzothiadiazolyl group, and a thiazolopyridyl group.

The arylalkyl group for $R^a$ to $R^f$ is preferably an alkyl group having one to six carbon atoms and substituted with any of those aryl groups, and more preferably an alkyl group having one to four carbon atoms and substituted with any of those aryl groups. Specific examples of the arylalkyl group include a benzyl group, a phenethyl group, a 3-phenylpropyl group, a 4-phenylbutyl group, a 1-phenylethyl group, and a 2-phenylpropan-2-yl group.

The heteroarylalkyl group for $R^a$ to $R^f$ is preferably an alkyl group having one to six carbon atoms and substituted with any of those heteroaryl groups, and more preferably an alkyl group having one to four carbon atoms and substituted with any of those heteroaryl groups. Specific examples of the heteroarylalkyl group include a pyridylmethyl group, a pyridylethyl group, an imidazolylmethyl group, an imidazolylethyl group, a pyrazolylmethyl group, a pyrazolylethyl group, a pyrazinylmethyl group, a pyrazinylethyl group, a pyridazinylmethyl group, a pyridazinylethyl group, a pyrimidinylmethyl group, a pyrimidinylethyl group, an oxazolylmethyl group, an oxazolylethyl group, a thiazolylmethyl group, and a thiazolylethyl group.

Examples of the substituent optionally possessed by the aryl group, heteroaryl group, arylalkyl group, and heteroarylalkyl group include a hydroxy group, an alkoxy group having one to four carbon atoms, a hydroxyalkyl group having one to four carbon atoms, an amino group, a mono- or dialkylamino group having an alkyl group having one to four carbon atoms, an alkoxycarbonyl group having an alkoxy group having one to four carbon atoms, and a halogen atom. Specific examples of the substituent include a hydroxy group, a methoxy group, an ethoxy group, a hydroxymethyl group, a hydroxyethyl group, an amino group, a monomethylamino group, a dimethylamino group, a methoxycarbonyl group, an ethoxycarbonyl group, a chlorine atom, and a fluorine atom.

$R^2$ is preferably a group represented by —$OR^a$, and $R^a$ in this case is preferably a hydrogen atom or an alkyl group having one to six carbon atoms. Preferred examples of $R^2$ include a hydroxy group, a methoxy group, and an ethoxy group.

$R^9$ is preferably a group represented by —$CH_2OR^d$, —$C(O)OR^d$, or —$C(O)NR^eR^f$, and more preferably a group represented by —$C(O)OR^d$ or —$C(O)NR^eR^f$. In the case that $R^9$ is a group represented by —$CH_2OR^d$, $R^d$ is preferably a hydrogen atom or an alkyl group having one to six carbon atoms. Specific examples of $R^d$ in this case include a hydrogen atom and a methyl group. In the case that $R^9$ is a group represented by —$C(O)OR^d$, $R^d$ is preferably a hydrogen atom, an alkyl group having one to six carbon atoms, an arylalkyl group, or a heteroarylalkyl group. Specific examples of $R^d$ in this case include a hydrogen atom, a methyl group, a pyridin-3-ylmethyl group, a pyridin-4- ylmethyl group, an oxazol-4-ylmethyl group, an oxazol-5-ylmethyl group, a thiazol-2-ylmethyl group, and a thiazol-5-ylmethyl group. In the case that $R^9$ is a group represented by —C(O)NR$^e$R$^f$, $R^e$ is preferably a hydrogen atom, and $R^f$ is preferably an arylalkyl group or a heteroarylalkyl group. Specific examples of $R^f$ in this case include a pyridin-3-ylmethyl group, a pyridin-4-ylmethyl group, an oxazol-4-ylmethyl group, an oxazol-5-ylmethyl group, a thiazol-2-ylmethyl group, and a thiazol-5-ylmethyl group.

Preferred examples of the compound represented by formula (1) above include a compound in which $R^1$ and $R^6$ are each independently an alkyl group, $R^2$ is a hydroxy group, $R^4$, $R^5$, $R^7$, and $R^8$ are each a hydrogen atom, $R^9$ is a group represented by —C(O)OR$^d$ or —C(O)NR$^e$R$^f$, $R^d$ is an arylalkyl group or a heteroarylalkyl group, $R^e$ is a hydrogen atom, and $R^f$ is an arylalkyl group or a heteroarylalkyl group. Preferred examples of the alkyl group, arylalkyl group, and heteroarylalkyl group are as described above.

In the case that the compound represented by formula (1) has an acidic functional group or a basic functional group, the compound may be in the form of a salt. In the case that the compound represented by formula (1) has an acidic functional group, for example, the compound may be in the form of an alkali metal salt (such as a sodium salt, a potassium salt), an alkaline earth metal (such as a calcium salt, a magnesium salt), or an ammonium salt. In the case that the compound represented by formula (1) has a basic functional group, the compound may be in the form of a salt with an inorganic acid such as hydrochloric acid and phosphoric acid, or in the form of a salt with an organic acid such as acetic acid, fumaric acid, and methanesulfonic acid.

<Production Method for Compound Represented by Formula (1)>

The compound represented by formula (1) can be produced, for example, through steps (A) to (L) in the following.

(A) Production of compound represented by formula (20) by asymmetric alkylation
(B) Production of compound represented by formula (19) by reduction
(C) Production of compound represented by formula (16) by oxidation and Mukaiyama Aldol reaction with Evans asymmetric auxiliary group
(D) Production of compound represented by formula (15) (Weinreb amide) from compound represented by formula (16)
(E) Production of compound represented by formula (14) by hydroxy group protection
(F) Production of compound represented by formula (11) by reduction and Wittig reaction
(G) Production of compound represented by formula (10) by reduction
(H) Production of compound represented by formula (8) by Wittig reaction
(I) Production of compound represented by formula (7) by reduction
(J) Production of compound represented by formula (6) by intramolecular Diels-Alder reaction
(K) Production of compound represented by formula (3) by Horner-Wadsworth-Emmons reaction and hydrolysis
(L) Production of compound represented by formula (1) from compound represented by formula (3)

The steps of the production method according to the present embodiment will be described in detail in the following. $R^1$ to $R^9$ and $R^a$ to $R^f$ in formulas are as described above.

[(A) Production of Compound Represented by Formula (20) by Asymmetric Alkylation]

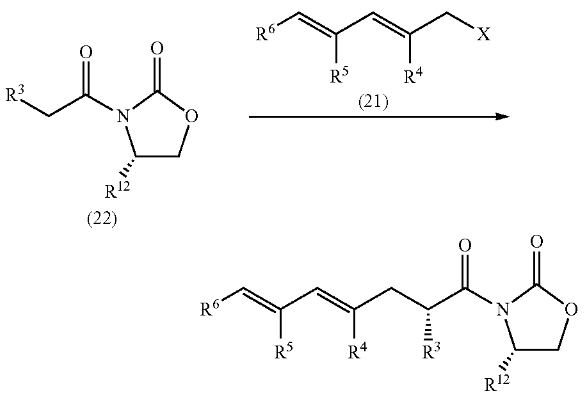

(22)

(21)

(20)

In formula (22), $R^{12}$ represents an alkyl group, an aryl group, or an arylalkyl group. The alkyl group for $R^{12}$ is preferably an alkyl group having one to six carbon atoms, and more preferably an alkyl group having one to four carbon atoms. The alkyl group may be linear, branched, or cyclic. Specific examples of the alkyl group include a methyl group, an ethyl group, an isopropyl group, an isobutyl group, and a cyclohexyl group. The aryl group for $R^{12}$ is preferably a monocyclic or polycyclic aromatic hydrocarbon group having 6 to 20 carbon atoms, and more preferably a monocyclic or polycyclic aromatic hydrocarbon group having 6 to 12 carbon atoms. Specific examples of the aryl group include a phenyl group, a naphthyl group, an anthryl group, phenanthryl group, and a pyrenyl group. The arylalkyl group for $R^{12}$ is preferably an alkyl group having one to six carbon atoms and substituted with any of those aryl groups, and more preferably an alkyl group having one to four carbon atoms and substituted with any of those aryl groups. Specific examples of the arylalkyl group include a benzyl group, a phenethyl group, a 3-phenylpropyl group, a 4-phenylbutyl group, a 1-phenylethyl group, and a 2-phenylpropan-2-yl group. Of these, $R^{12}$ is particularly preferably a benzyl group, a phenyl group, or an isopropyl group.

In formula (21), X represents a halogen atom (such as a fluorine atom, a chlorine atom, a bromine atom, an iodine atom).

The compound represented by formula (20) (optically active isoxazolidine derivative) can be produced by allowing a base to act on the compound represented by formula (22) to generate an enolate, and reacting this with the compound represented by formula (21) (halogenated product) as an alkylating agent. For the base, lithium diisopropylamide, lithium bis(trimethylsilyl)amide, sodium bis(trimethylsilyl) amide, potassium bis(trimethylsilyl)amide, and the like can be used. Furthermore, tetrabutylammonium iodide may be added as a catalyst. The reaction is performed in an organic solvent such as tetrahydrofuran and ether. The reaction temperature is preferably about −78° C. to room temperature. After the reaction, the target product is collected, and purified by column chromatography or the like.

The configuration of $R^3$ in the compound represented by formula (20) is determined by the configuration of $R^{12}$ in the compound represented by formula (22).

[(B) Production of Compound Represented by Formula (19) by Reduction]

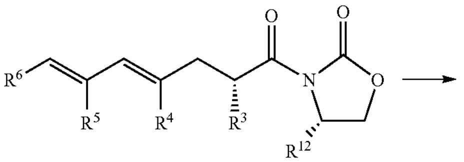

(20)

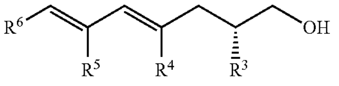

(19)

The compound represented by formula (20) (optically active isoxazolidine derivative) can be converted, without deteriorating the optical purity, into the compound represented by formula (19) (alcohol) by treating with a reducing agent. For the reducing agent, $LiAlH_4$, $LiBH_4$-EtOH, $NaH_2Al(OCH_2CH_2OMe)_2$, and the like can be used. The reaction is performed in an organic solvent such as tetrahydrofuran and ether. The reaction temperature is preferably about 0° C. to room temperature. After the reaction, the target product is collected, and purified by column chromatography or the like.

[(C) Production of Compound Represented by Formula (16) by Oxidation and Mukaiyama Aldol Reaction with Evans Asymmetric Auxiliary Group]

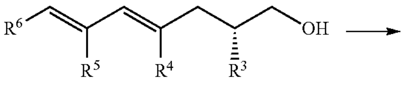

(19)

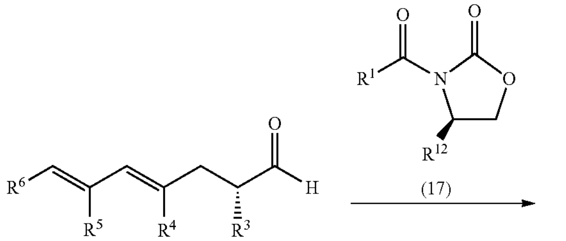

(17)

(18)

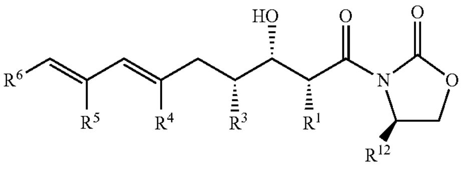

(16)

First, the compound represented by formula (19) (alcohol) is oxidized to produce a compound represented by formula (18) (aldehyde). For the oxidation reaction, a weak oxidizing agent such as dimethyl sulfoxide, tetrapropylammonium perruthenate, and Dess-Martin periodinane can be used. The reaction is performed in an organic solvent such as methylene chloride. The reaction temperature is preferably about 0° C. to room temperature. The resulting compound represented by formula (18) may be directly used for the subsequent reaction without being isolated.

Subsequently, the compound represented by formula (16) can be produced by subjecting the compound represented by formula (18) and the compound represented by formula (17) to Mukaiyama Aldol reaction in the presence of boron triflate and an amine.

In formula (17), $R^{12}$ as described in formula (22). For the amine, triethylamine, 2,6-lutidine, and the like can be used. The reaction is performed in an organic solvent such as methylene chloride, tetrahydrofuran, and 1,2-dimethoxyethane. The reaction temperature is preferably about −78° C. to 0° C. After the reaction, the target product is collected, and purified by column chromatography or the like.

[(D) Production of Compound Represented by Formula (15) (Weinreb Amide) from Compound Represented by Formula (16)]

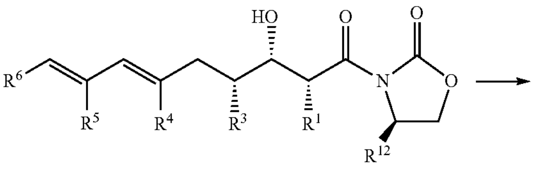

(16)

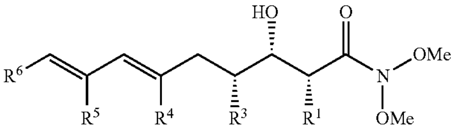

(15)

The compound represented by formula (16) can be converted into the compound represented by formula (15) (Weinreb amide) with ease by reacting with N,O-dimethylhydroxylamine. In formula (15), Me represents a methyl group. The reaction is performed in an organic solvent such as tetrahydrofuran. The reaction temperature is preferably about 0° C. After the reaction, the target product is collected, and purified by column chromatography or the like.

[(E) Production of Compound Represented by Formula (14) by Hydroxy Group Protection]

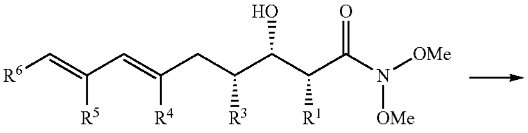

(15)

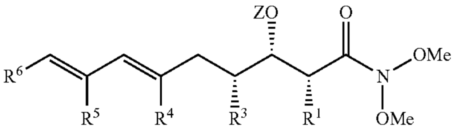

(14)

In formula (14), Z represents a protecting group for a hydroxy group. Z is preferably a protecting group that is capable of protecting hydroxy groups under temperate conditions and stable under alkaline conditions. Preferred examples of the protecting group include trialkylsilyl groups such as a trimethylsilyl group, a triethylsilyl group, and a tert-butyldimethylsilyl group.

The protection of a hydroxy group is preferably performed by reacting with trialkylsilyl triflate or the like in an organic solvent such as methylene chloride with use of the weak base 2,6-lutidine or the like as a catalyst. The reaction temperature is preferably about 0° C. After the reaction, the target product is collected, and purified by column chromatography or the like.

[(F) Production of Compound Represented by Formula (11) by Reduction and Wittig Reaction]

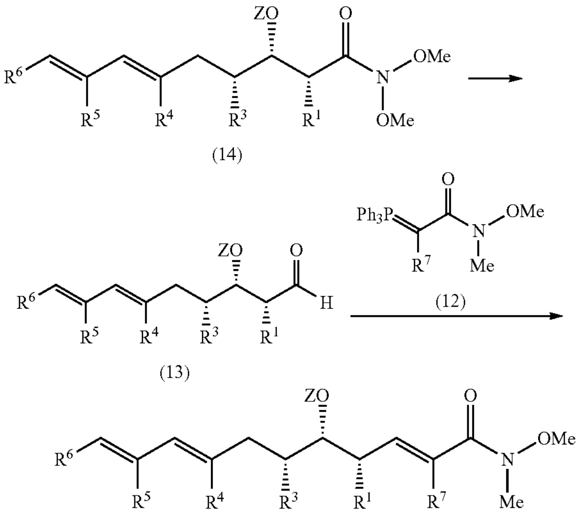

(14)

(13)

(12)

(11)

First, the compound represented by formula (14) (amide) is reduced to produce the compound represented by formula (13) (aldehyde). At that time, use of diisobutylaluminum hydride as a reducing agent is preferred because the reduction can be stopped at the stage of aldehyde formation. The reaction is performed in an organic solvent such as tetrahydrofuran, toluene, hexane, and methylene chloride. The reaction temperature is preferably about −78° C. to 0° C. After the reaction, the target product is collected.

Subsequently, the compound represented by formula (11) can be produced by subjecting the compound represented by formula (13) (aldehyde) and the compound represented by formula (12) (Wittig reagent) to Wittig reaction. The reaction is performed in an organic solvent such as methylene chloride. The reaction temperature is preferably about 35° C. After the reaction, the target product is collected, and purified by column chromatography or the like.

[(G) Production of Compound Represented by Formula (10) by Reduction]

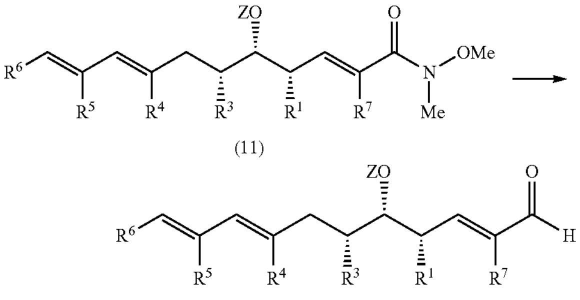

(11)

(10)

The compound represented by formula (10) (aldehyde) can be produced by reducing the compound represented by formula (11) (amide) in the same manner as in step (F). The reaction conditions and others may be the same as those in step (F).

[(H) Production of Compound Represented by Formula (8) by Wittig Reaction]

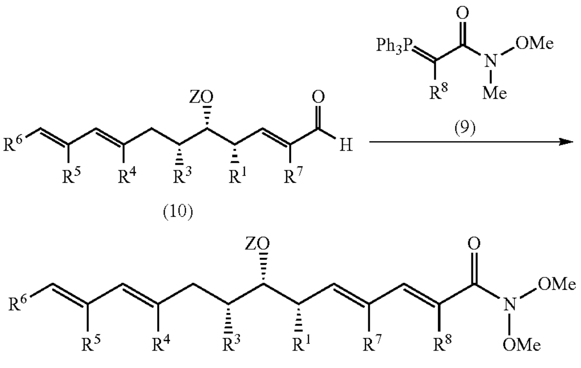

(9)

(10)

(8)

The compound represented by formula (8) can be produced by subjecting the compound represented by formula (10) (aldehyde) and the compound represented by formula (9) (Wittig reagent) to Wittig reaction in the same manner as in step (F). The reaction conditions and others may be the same as those in step (F).

[(I) Production of Compound Represented by Formula (7) by Reduction]

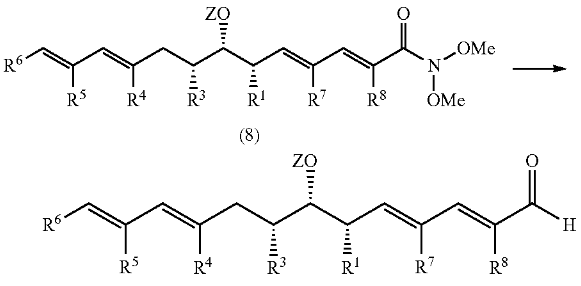

(8)

(7)

The compound represented by formula (7) (aldehyde) can be produced by reducing the compound represented by formula (8) (amide) in the same manner as in step (F). The reaction conditions and others may be the same as those in step (F).

[(J) Production of Compound Represented by Formula (6) by Intramolecular Diels-Alder Reaction]

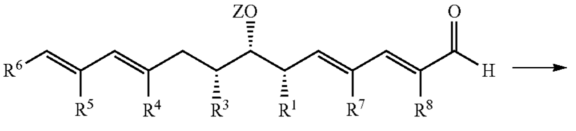

(7)

-continued

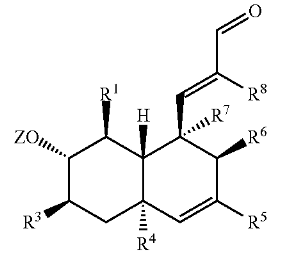

(6)

Intramolecular Diels-Alder reaction is promoted by a driving force generated by conversion of an 8π system in a molecule with open chain structure into a more stable 4π+4σ system in a molecule with cyclic structure. It is preferable to use a catalyst such as diethylaluminum chloride for the reaction. The reaction is performed in an organic solvent such as methylene chloride. The reaction temperature is preferably about −78° C. to room temperature. The crude product contains compounds having different conformations in addition to the compound represented by formula (6), and hence the crude product is purified by thin-layer chromatography or the like and the target product is collected.

[(K) Production of Compound Represented by Formula (3) by Horner-Wadsworth-Emmons Reaction and Hydrolysis]

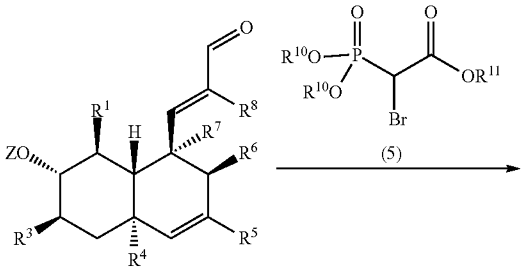

(6) (5)

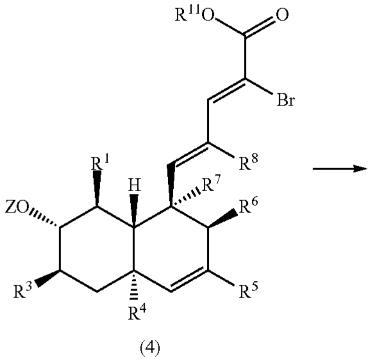

(4)

-continued

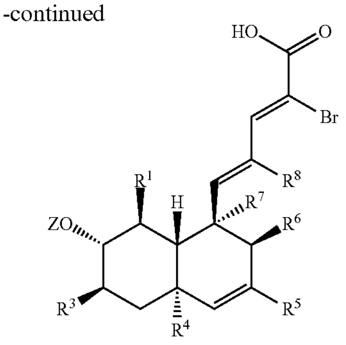

(3)

In formula (5), $R^{10}$ and $R^{11}$ each independently represent an alkyl group. The alkyl group for $R^{10}$ and $R^{11}$ is preferably an alkyl group having one to six carbon atoms, and more preferably an alkyl group having one to four carbon atoms. The alkyl group may be linear, branched, or cyclic. Specific examples of the alkyl group include a methyl group, an ethyl group, an isopropyl group, an isobutyl group, and a cyclohexyl group, and a methyl group and an ethyl group are preferred.

First, the compound represented by formula (4) is produced by subjecting the compound represented by formula (6) and the compound represented by formula (5) to Horner-Wadsworth-Emmons reaction. Specifically, a base is allowed to act on the compound represented by formula (5) (alkylphosphonate) to generate a carboanion, which is reacted with the compound represented by formula (6) (aldehyde) to produce the compound represented by formula (4) (alkene). It is preferable to use lithium bis(trimethylsilyi) amide, lithium diisopropylamide, or the like for the base. The reaction is performed in an organic solvent such as tetrahydrofuran and methylene chloride. The reaction temperature is preferably about −78° C. to room temperature. The crude product contains compounds having different conformations in addition to the compound represented by formula (4), and hence the crude product is purified by thin-layer chromatography or the like and the target product is collected.

Subsequently, the compound represented by formula (3) can be produced by hydrolyzing the compound represented by formula (4). Hydrolysis with a hydroxy group kept protected can be achieved by performing hydrolysis with a base catalyst such as sodium hydroxide and lithium hydroxide as appropriate.

[(L) Production of Compound Represented by Formula (1) from Compound Represented by Formula (3)]

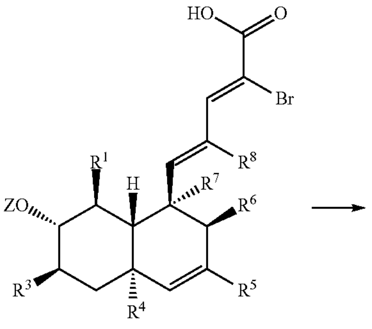

(3)

-continued

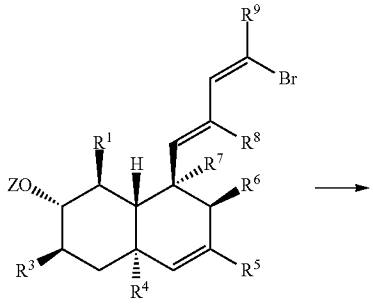

(2)

-continued

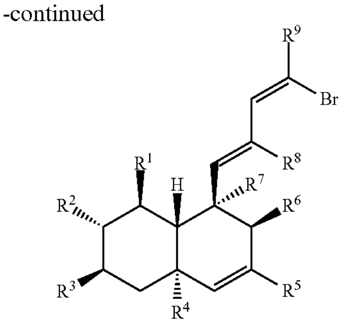

(1)

After the compound represented by formula (2) is produced by converting the carboxy group of the compound represented by formula (3) into $R^9$, the compound represented by formula (1) can be produced by converting —OZ of the compound represented by formula (2) into $R^2$.

The conversion of the compound represented by formula (3) into the compound represented by formula (2) can be performed with a method used in common organic synthesis, and esterification, amidation, halogenation, acid anhydride formation, etherification, amination, oxidation, reduction, coupling reaction, protection, deprotection, and others can be variously combined therefor as appropriate. A reaction example is shown in the following.

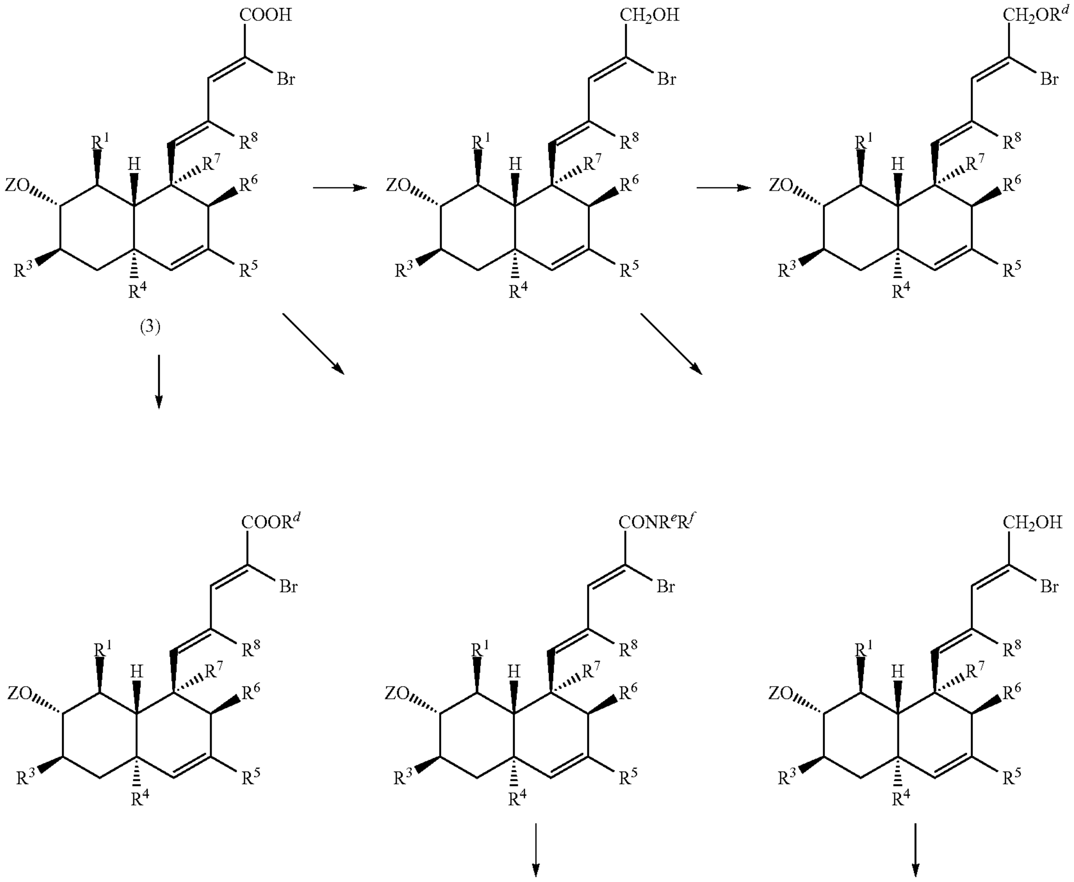

(3)

-continued

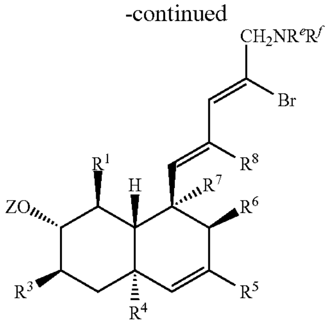

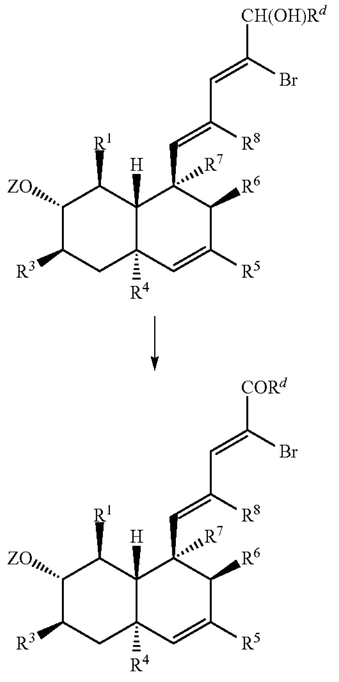

A compound in which $R^9$ is —$CH_2OR^d$ can be obtained by reducing the carboxy group of the compound represented by formula (3) with a reducing agent such as lithium aluminium hydride and performing Williamson synthesis to react with a halogenated alkyl represented by $R^dX$. A compound in which is —$C(O)NR^eR^f$ can be obtained by subjecting the carboxy group of the compound represented by formula (3) to dehydration condensation reaction with an amine represented by $NHR^eR^f$. A compound in which $R^9$ is —$CH_2NR^eR^f$ can be obtained by reducing the compound in which $R^9$ is —$C(O)NR^eR^f$ with a reducing agent such as lithium aluminium hydride. A compound in which $R^9$ is —$C(O)OR^d$ can be obtained by subjecting the carboxy group of the compound represented by formula (3) to dehydration condensation reaction with an alcohol represented by $R^dOH$. A compound in which $R^9$ is —$CH(OH)R^d$ can be obtained by reducing the carboxy group of the compound represented by formula (3) into a hydroxymethyl group, then oxidizing it into a formyl group, and reacting it with a Grignard reagent represented by $R^dMgX$. Thereafter, a compound in which $R^9$ is —$COR^d$ can be obtained by oxidizing the compound in which $R^9$ is —$CH(OH)R^d$.

The conversion of the compound represented by formula (2) into the compound represented by formula (1) can be performed with a method used in common organic synthesis, and esterification, etherification, halogenation, amination, oxidation, reduction, protection, deprotection, and others can be variously combined therefor as appropriate. If a hydroxy group, a carboxy group, an amino group, or another group is introduced to $R^9$ to form an intermediate to be converted, protection and deprotection of such a group can be performed as appropriate, if necessary for the subsequent reaction. A reaction example is shown in the following.

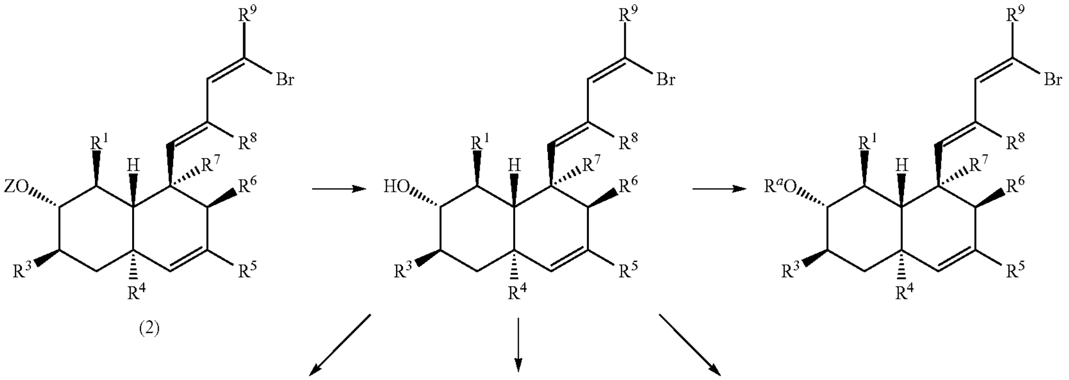

(2)

-continued

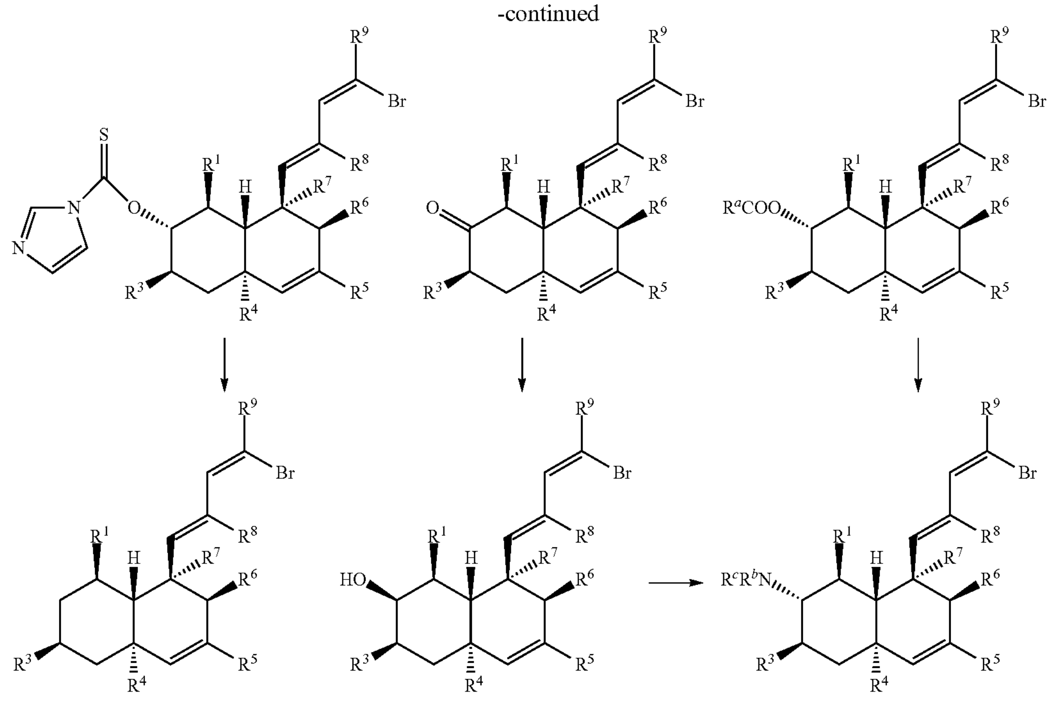

First, protecting group Z is eliminated from —OZ of the compound represented by formula (2) to form a hydroxy group, which is then converted into various groups. For example, a compound in which $R^2$ is —$OR^d$ can be obtained by performing Williamson synthesis to react the hydroxy group with a halogenated alkyl represented by $R^aX$. A compound in which $R^2$ is —$O(CO)R^a$ can be obtained by subjecting the hydroxy group to dehydration condensation reaction with a carboxylic acid represented by $R^aCOOH$. If the alcohol having a hydroxy group is oxidized into a ketone and the ketone is reduced with a reducing agent such as diisobutylaluminum hydride, the hydride attack proceeds from the opposite side of the substituents $R^1$ and $R^3$, as a result giving a sterically inverted alcohol. Activation of the hydroxy group of this alcohol with diethyl azodicarboxylate and triphenylphosphine and subsequent Mitsunobu reaction to react with $R^bR^cNH$ allow a sterically re-inverted amino group to be introduced, giving a compound in which $R^2$ is —$NR^cR^d$. A compound in which $R^2$ is a hydrogen atom can be obtained by reacting the hydroxy group with 1,1'-thiocarbonyldiimidazol to convert it into thiocarbamate and then performing radical reduction with tributyltin hydride and azobisisobutvronitrile.

<Pharmaceutical Composition>

The pharmaceutical composition according to the present embodiment contains the compound represented by formula (1) above and a pharmaceutically acceptable carrier.

The compound represented by formula (1), as with the case of its analog, M-COPA, exhibits cell proliferation inhibitory action against various cancers. Accordingly, the pharmaceutical composition according to the present embodiment is applicable as a pharmaceutical composition for treating various cancers. The term "treat" encompasses not only abolishing or alleviating a symptom of a disease but also reducing the degree of progression of a symptom.

In particular, the compound represented by formula (1), as with the case of its analog, M-COPA, is capable of inhibiting, for example, the translocation of receptor tyrosine kinases (such as KIT, FLT3, FGFR3, EGFR, MET) to a Golgi apparatus or a cellular membrane via reducing the endoplasmic reticulum-Golgi apparatus transport of them. Accordingly, the pharmaceutical composition according to the present embodiment is effective also for treatment of cancers with activation mutation of KIT (e.g., gastrointestinal stromal tumor, mast cell leukemia, acute myelogenous leukemia); cancers with high tyrosine kinase receptor expression that are highly expressing FLT3, FGFR3, EGFR, MET, or the like (e.g., acute myelogenous leukemia, multiple myeloma, lung adenocarcinoma, gastric cancer); cancers with tyrosine kinase receptor inhibitor resistance (e.g., imatinib-resistant acute myelogenous leukemia, imatinib-resistant gastrointestinal stromal tumor, multiple myeloma, gefitinib-resistant and osimertinib-resistant non-small cell lung adenocarcinomas); and others.

Examples of the pharmaceutically acceptable carrier include organic or inorganic carriers conventionally used as formulation materials. The carrier is added as a diluent, a lubricant, a binder, a disintegrator, or the like for solid formulations, and as a solvent, a solubilizer, a suspending agent, an isotonic agent, a buffer, or the like for liquid formulations. The pharmaceutical composition may contain a formulation excipient such as a preservative, an antioxidant, and a coloring agent.

The pharmaceutical composition may be in any dosage form without limitation. Examples of the dosage form of the pharmaceutical composition include oral preparations such as tablets, capsules, emulsions, and suspensions; and parenteral preparations such as injections, infusions, and topical agents.

The dose of the pharmaceutical composition is appropriately determined depending on the subject of administration, the route of administration, the target disease, symptoms, and others.

EXAMPLES
Hereinafter, Examples of the present invention will be described, but the scope of the present invention is not limited to those Examples.
In Examples below, compounds RS1 to RS10 shown below were produced as the compound represented by formula (1) above. In addition, M-COPA was prepared for comparison.
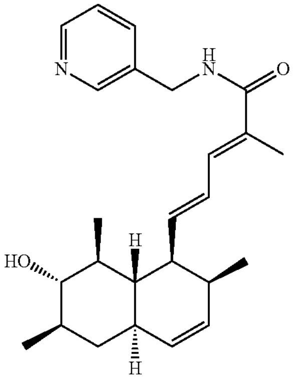
M-COPA
RS1
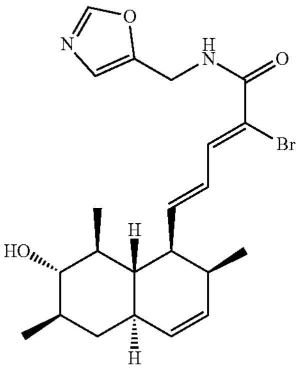
RS2
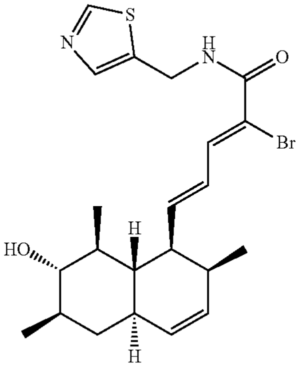
-continued
RS3
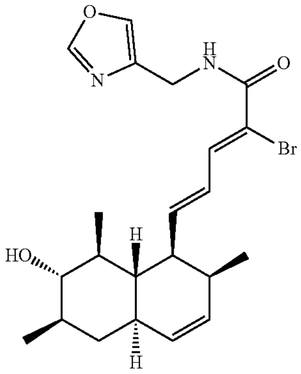
RS4
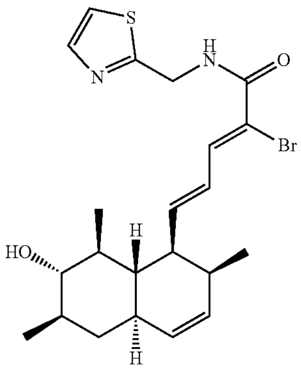
RS5
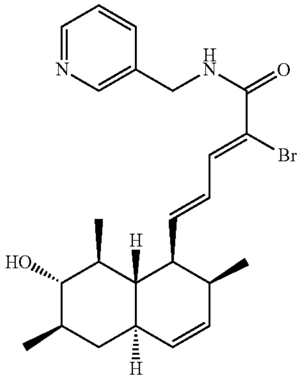
RS6
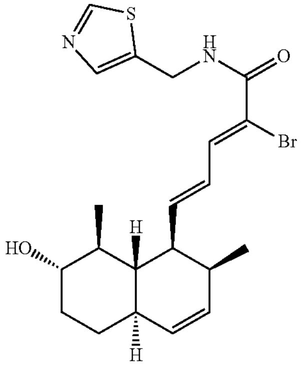

-continued

RS7

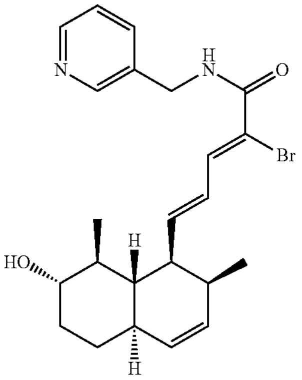

RS8

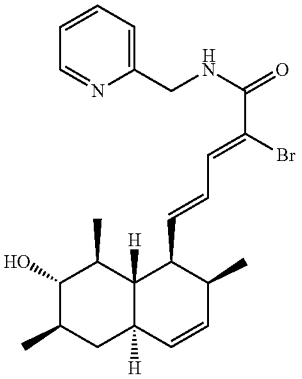

RS9

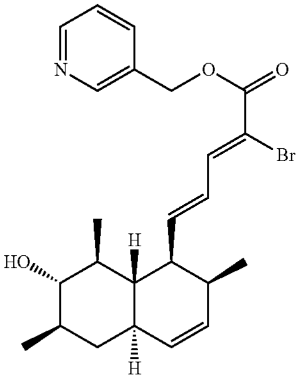

RS10

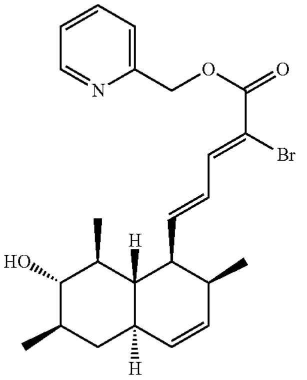

Synthesis Example 1: Synthesis of (2Z,4E)-2-bromo-5-((1'S,2'S,4'aR,6'R,7'S,8'S,8'aS)-7'-hydroxy-2',6',8'-trimethyl-1',2',4'a,5',6',7',8',8'a-octahydronaphthalen-1'-yl)-N-(oxazol-5"-ylmethyl)penta-2,4-dienamide (compound RS1)

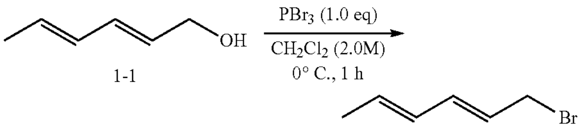

1-1

1-2

Preparation of (2E,4E)-1-bromohexa-2,4-diene (compound 1-2)

To a methylene chloride solution (51 mL) containing 2,4-hexadien-1-ol (10.0 g, 102 mmol), phosphorus tribromide (9.7 mL, 102 mmol) was added dropwise at 0° C., and stirring was performed for 1 hour. After dilution by adding water to the reaction system at 0° C., an organic layer was separated from the reaction mixture solution. The organic layer was dried over anhydrous sodium sulfate, and then filtered and concentrated under reduced pressure to afford a crude product. With pre-cooled silica gel, partial purification by gel filtration (eluent: hexane/ethyl acetate=10/1; the eluent used is previously cooled to 0° C.) was performed. Filtration and concentration under reduced pressure gave a crude product of compound 1-2. This crude product was directly used for the subsequent reaction without purification.

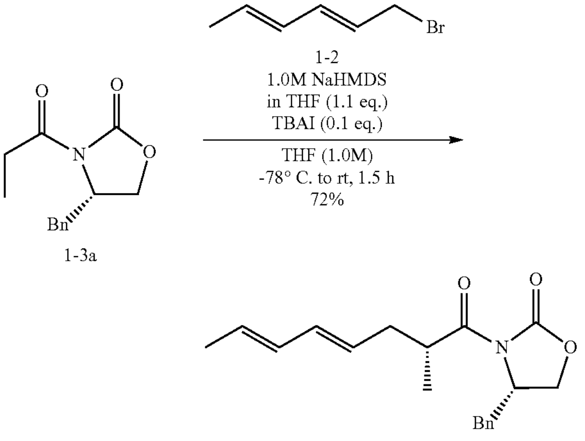

1-3a 1-4

[Asymmetric Alkylation]

To a tetrahydrofuran solution (39 mL) containing (S)-4-benzyl-3-propionvloxazolidin-2-one (compound 1-3a) (9.0 g, 38.7 mmol), a tetrahydrofuran solution of sodium bis (trimethylsilyl)amide (1.0 M, 43 mL, 43.0 mmol) was added dropwise at −78° C. After the reaction mixture solution was stirred for 15 minutes, (2E,4E)-1-bromohexa-2,4-diene (compound 1-2) (12.5 g, 77.4 mmol) and tetrabutylammonium iodide (1.48 g, 4.0 mmol) were added thereto, the temperature was increased to room temperature, and stirring was performed for 1.5 hours. Saturated aqueous solution of ammonium chloride was added to the reaction system at 0° C. to terminate the reaction, ethyl acetate was added to separate an organic layer, and extraction with ethyl acetate was then performed for the aqueous layer. The organic layers were combined and the resultant was dried over anhydrous sodium sulfate, and then filtered and concentrated under reduced pressure to afford a crude product. The crude product obtained was purified by column chromatography (eluent: hexane/ethyl acetate=7/1) to afford (S)-4-benzyl-3-((R,4'E,6'E)-2'-methylocta-4',6'-dienoyi)oxazolidin-2-one (compound 1-4) (8.8 g, 72%).

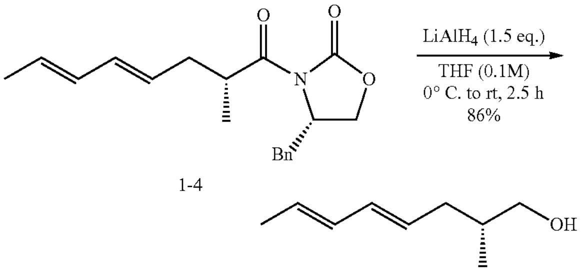

1-4

1-5

[Reduction]

To a tetrahydrofuran solution (133 mL) containing lithium aluminium hydride (3.4 g, 89.6 mmol), a tetrahydrofuran solution (66 mL) of (S)-4-benzyl-3-((R,4'E,6'E)-2'-methyl-octa-4',6'-dienoyl)oxazolidin-2-one (compound 1-4) (18.7 g, 59.7 mmol) was added dropwise at 0° C., and the reaction mixture solution was stirred at room temperature for 2.5 hours. Methanol and 1.0 M hydrochloric acid were added to the reaction system at 0° C. to terminate the reaction, ethyl acetate was added to separate an organic layer, and extraction with ethyl acetate was then performed for the aqueous layer. The organic layers were combined and the resultant was dried over anhydrous sodium sulfate, and then filtered and concentrated under reduced pressure to afford a crude product. The crude product obtained was purified by column chromatography (eluent: hexane/ethyl acetate=5/1) to afford (R,4E,6E)-2-methylocta-4,6-dien-1-ol (compound 1-5) (7.2 g, 86%).

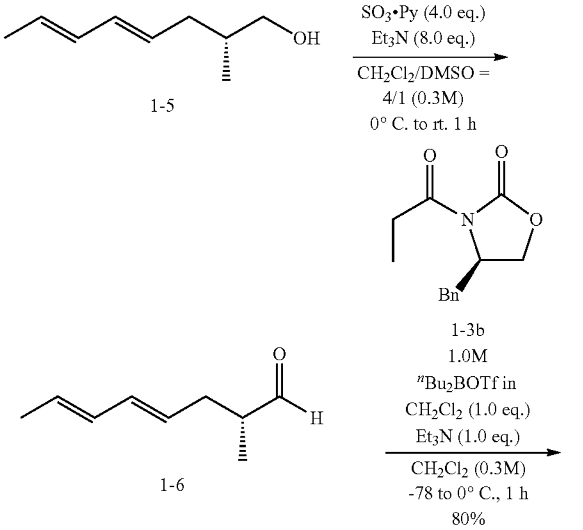

1-5

1-3b 1-6

-continued

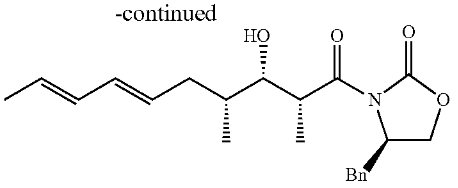

1-7

[Oxidation]

To a methylene chloride solution (131 mL) containing (R,4E,6E)-2-methylocta-4,6-dien-1-ol (compound 1-5) (6.9 g, 49.3 mmol), dimethyl sulfoxide (32.8 mL, 462 mmol) and triethylamine (54.6 mL, 394 mmol) were added at room temperature. After the temperature of the reaction mixture solution was set to 0° C., sulfur trioxide-pyridine complex (31.4 g, 197 mmol) was added at room temperature, and the reaction mixture was stirred for 1 hour. The reaction mixture solution containing a crude product of compound 1-6 was directly used for the subsequent reaction without purification.

[Mukaiyama Aldol Reaction with Evans Asymmetric Auxiliary Group]

To a methylene chloride solution (164 mL) containing (R)-4-benzyl-3-propionyloxazolidin-2-one (compound 1-3b) (11.5 g, 49.3 mmol), a methylene chloride solution of dibutylboron trifluoromethanesulfonate (49.3 mL, 49.3 mmol) and triethylamine (6.8 mL, 49.3 mmol) were added at 0° C., and stirring was performed for 10 minutes. After the temperature of the reaction mixture solution was set to −78° C., the reaction mixture solution containing a crude product of compound 1-6 was added by cannulation, stirring was performed for 30 minutes, the temperature was increased to 0° C., and stirring was further performed for 1 hour. Phosphate buffer solution (pH 7) was added to the reaction system at 0° C. to terminate the reaction, methylene chloride was added to separate an organic layer, and extraction with methylene chloride was then performed for the aqueous layer. The organic layers were combined and the resultant was dried over anhydrous sodium sulfate, and then filtered and concentrated under reduced pressure to afford a crude product. The crude product obtained was purified by column chromatography (eluent: hexane/ethyl acetate=10/1→3/1) to afford (R)-4-benzyl-3-((2'R,3'S,4'R,6'E,8'E)-3'-hydroxy-2',4'-dimethyldeca-6',8'-dienoyl)oxazolidin-2-one (compound 1-7) (14.6 g, two-step yield: 80%).

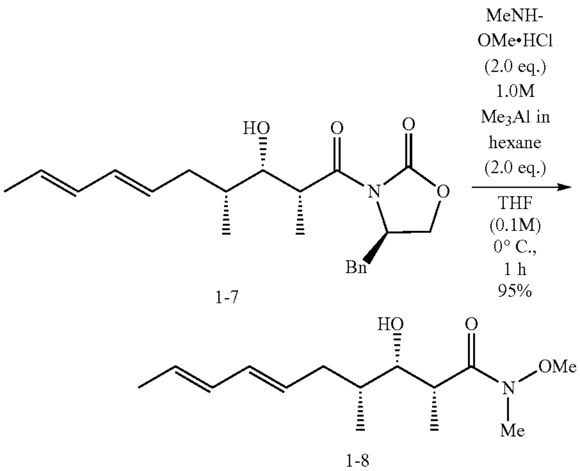

1-7

1-8

[Conversion into Weinreb Amide]

To a tetrahydrofuran solution (230 mL) of N,O-dimethylhydroxylamine hydrochloride (6.83 g, 70.0 mmol), a n-hexane solution of trimethylaluminum (1.0 M, 70 mL, 70.0 mmol) was added at 0° C., the reaction solution was stirred at 0° C. for 15 minutes, the temperature was then increased to room temperature, and the reaction solution was stirred for 15 minutes. To the reaction mixture solution, a tetrahydrofuran solution (120 mL) of (R)-4-benzyl-3-((2'R, 3'S,4'R,6'E,8'E)-3'-hydroxy-2',4'-dimethyldeca-6',8'-dienoyl)oxazolidin-2-one (compound 1-7) (13.0 g, 35.0 mmol) was added at 0° C., and stirring was performed for 15 minutes. Saturated aqueous solution of potassium sodium tartrate was added to the reaction system at 0° C. to terminate the reaction, ethyl acetate was added to separate an organic layer, and extraction with ethyl acetate was then performed for the aqueous layer. The organic layers were combined and the resultant was dried over anhydrous sodium sulfate, and then filtered and concentrated under reduced pressure to afford a crude product. The crude product obtained was purified by column chromatography (eluent: hexane/ethyl acetate=3/1→1/1) to afford (2R,3S, 4R,6E,8E)-3-hydroxy-N-methoxy-N,2,4-trimethyldeca-6,8-dienamide (compound 1-8) (8.5 g, 95%).

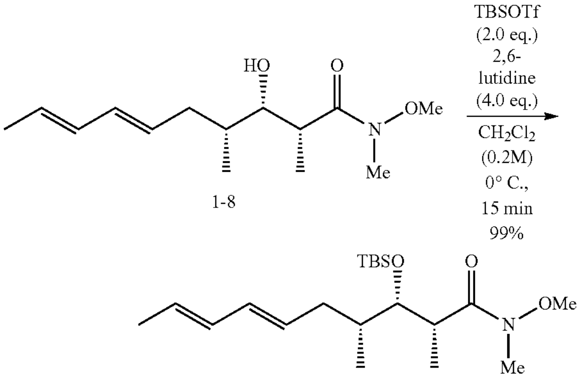

1-8

1-9

[Hydroxy Group Protection]

To a methylene chloride solution (170 mL) containing (2R,3S,4R,6E,8E)-3-hydroxy-N-methoxy-N,2,4-trimethyldeca-6,8-dienamide (compound 1-8) (8.63 g, 33.8 mmol), 2,6-lutidine (15.8 mL, 135 mmol) and tert-butyldimethylsilyl triflate (15.5 mL, 67.6 mmol) were added at 0° C., and the reaction mixture solution was stirred at 0° C. for 15 minutes. Saturated aqueous solution of ammonium chloride was added to the reaction system at 0° C. to terminate the reaction, methylene chloride was added to separate an organic layer, and extraction with methylene chloride was then performed for the aqueous layer. The organic layers were combined and the resultant was dried over anhydrous sodium sulfate, and then filtered and concentrated under reduced pressure to afford a crude product. The crude product obtained was purified by column chromatography (eluent: hexane/ethyl acetate=20/1→5/1) to afford (2R, 3S, 4R, 6E, 8E)-3-((tert-butyldimethylsily)oxy-N-methoxy-N,2, 4-trimethyldeca-6,8-dienamide (compound 1-9) (12.4 g, 99%).

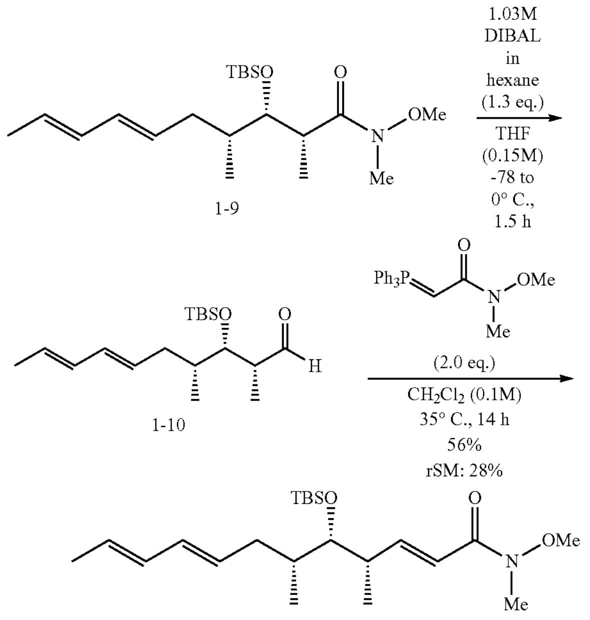

1-9

1-10

1-11

[Reduction]

To a tetrahydrofuran solution (5.7 mL) containing (2R, 3S, 4R, 6E, 8E)-3-((tert-butyldimethylsilyl)oxy)-N-methoxy-N,2,4-trimethyldeca-6,8-dienamide (compound 1-9) (211 mg, 0.570 mmol), a n-hexane solution of diisobutylaluminum hydride (1.03 M, 0.72 mL, 0.74 mmol) was added at −78° C., the temperature was increased to 0° C., and stirring was performed for 1.5 hours. Methanol and saturated aqueous solution of potassium sodium tartrate were added to the reaction system at 0° C. to terminate the reaction, ethyl acetate was added to separate an organic layer, and extraction with ethyl acetate was then performed for the aqueous layer. The organic layers were combined and the resultant was dried over anhydrous sodium sulfate, and then filtered and concentrated under reduced pressure to afford a crude product of compound 1-10. This crude product was directly used for the subsequent reaction without purification.

[Wittig Reaction]

To a methylene chloride solution (5.7 mL) containing the crude product of compound 1-10, N-methoxy-N-methyl 2-(triphenyl-$\lambda^5$-phosphanylidene) acetamide (414 mg, 1.140 mmol) was added at room temperature, the temperature was increased to 35° C., and stirring was performed for 16 hours. The reaction mixture solution was concentrated under reduced pressure to afford a crude product. The crude product obtained was purified by column chromatography (eluent: hexane/ethyl acetate=4/1) to afford (2E,4S,5S,6R, 8E,10E)-5-((tert-butyldimethylsilyfloxy)-N-methoxy-N,4, 6-trimethyldodeca-2,8,10-trienamide (compound 1-11) (132 mg, two-step yield: 56%). At that time, 59.4 mg (28%) of compound 1-10 was collected. The physical property values of compound 1-10 and compound 1-11 are as follows.

(2R,3S,4R,6E,8E)-3-((tert-butyldimethylsilyl)oxy)-2,4-dimethyldeca-6,8-dienal (compound 1-10)

$^1$H NMR (400 MHz, $CDCl_3$): δ 9.81 (d, J=0.8 Hz, 1H, CHO), 6.07-5.93 (m, 2H, H-7, H-8), 6.07-5.93 (m, 1H, H-9), 5.50-5.40 (m, 1H, H-6), 4.00 (dd, J=4.8, 4.0 Hz, 1H, H-3), 2.58-2.47 (m, 1H, H-2), 2.27-2.16 (m, 1H, H-5), 1.94-1.83 (m, 1H, H-5), 1.07 (d, J=7.2 Hz, 1H, 2-Me), 0.89 (s, 9H, TBS), 0.84 (d, J=6.8 Hz, 3H, 4-Me), 0.08 (s, 3H, TBS), 0.03 (s, 3H, TBS).

(2E,4S,5S,6R,8E,10E)-5-((tert-butyldimethylsilyl) oxy)-N-methoxy-N,4,6-trimethyldodeca-2,8,10-trienamide (compound 1-11)

$^1$H NMR (400 MHz, $CDCl_3$): δ 6.94 (dd, J=15.6, 8.8 Hz, 1H, H-3), 6.34 (d, J=15.6 Hz, 1H, H-2), 6.04-5.90 (m, 2H, H-9, H-10), 5.61-5.50 (m, 1H, H-11), 5.50-5.40 (m, 1H, H-8), 3.67 (s, 3H, NMe), 3.50 (dd, J=6.4, 3.2 Hz, 1H, H-5), 3.22 (s, 3H, OMe), 2.61-2.47 (m, 1H, H-4), 1.94-1.84 (m, 1H, H-7), 1.71 (d, J=6.8 Hz, 3H, H-12), 1.66-1.56 (m, 1H, H-6), 1.05 (d, J=5.6 Hz, 3H, 4-Me), 0.90 (s, 9H, TBS), 0.81 (d, J=6.8 Hz, 3H, 6-Me), 0.04 (s, 3H, TBS), 0.04 (s, 3H, TBS).

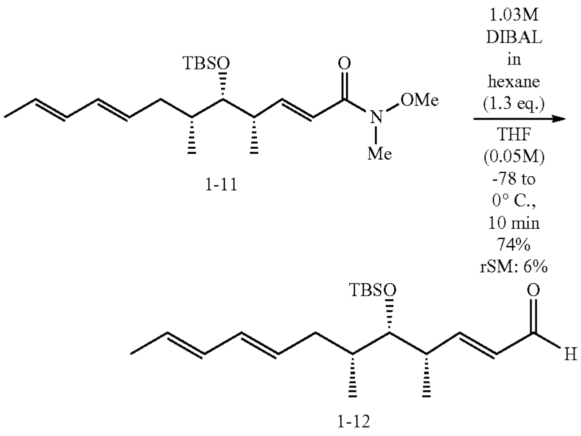

1-11
1-12

[Reduction]

To a tetrahydrofuran solution (6.6 mL) containing (2E, 4S,5S,6R,8E,10E)-5-((tert-butyldimethylsilyl)oxy)-N-methoxy-N,4,6-trimethyldodeca-2,8,10-trienamide (compound 1-11) (132 mg, 0.332 mmol), a n-hexane solution of diisobutylaluminum hydride (1.03 M, 0.42 mL, 0.43 mmol) was added at −78° C., the temperature was increased to 0° C., and stirring was performed for 10 minutes. Methanol and saturated aqueous solution of potassium sodium tartrate were added to the reaction system at 0° C. to terminate the reaction, ethyl acetate was added to separate an organic layer, and extraction with ethyl acetate was then performed for the aqueous layer. The organic layers were combined and the resultant was dried over anhydrous sodium sulfate, and then filtered and concentrated under reduced pressure to afford a crude product. The crude product obtained was purified by thin-layer chromatography (eluent: hexane/ethyl acetate=4/1) to afford (2E,4S,5S,6R,8E,10E)-5-((tert-butyldimethylsilyl)oxy)-4,6-dimethyldodeca-2,8,10-trienal (compound 1-12) (82.8 mg, 74%). At that time, 7.5 mg (6%) of compound 1-11 was collected. The physical property values of compound 1-12 are as follows.

(2E,4S,5S,6R,8E,10E)-5-((tert-butyldimethylsilyl) oxy)-4,6-dimethyldodeca-2,8,10-trienal (compound 1-12)

$^1$H NMR (400 MHz, $CDCl_3$): δ 9.51 (d, J=7.6 Hz, 1H, CHO), 6.94 (dd, J=16.0, 6.8 Hz, 1H, H-3), 6.08 (ddd, J=16.0, 7.6, 1.6 Hz, 1H, H-2), 6.03-5.93 (m, 2H, H-9, H-10), 5.64-5.52 (m, 1H, H-11), 5.49-5.40 (m, 1H, H-8), 3.63 (dd, J=6.0, 2.8 Hz, 1H, H-5), 2.66 (dqd, J=6.8, 6.8, 6.4 Hz, 1H, H-4), 2.17-2.08 (m, 1H, H-7), 1.97-1.85 (m, 1H, H-7), 1.72 (d, J=6.4 Hz, 3H, H-12), 1.64-1.55 (m, 1H, H-6), 1.09 (d, J=6.8 Hz, 3H, 4-Me), 0.92 (s, 9H, TBS), 0.79 (d, J=7.6 Hz, 3H, 4-Me), 0.07 (s, 3H, TBS), 0.05 (s, 3H, TBS).

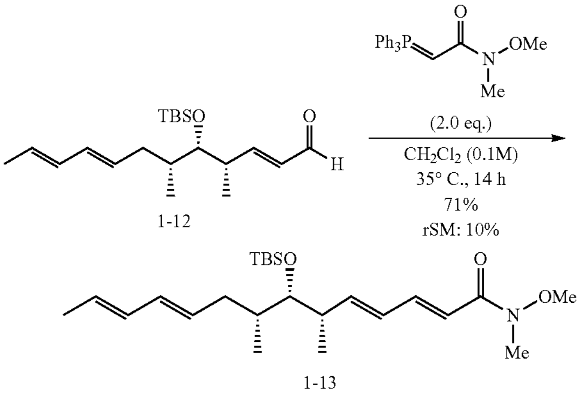

1-12
1-13

[Wittig Reaction]

To a methylene chloride solution (2.5 mL) containing (2E,4S,5S,6R,8E,10E)-5-((tert-butyldimethylsilyl)oxy)-4,6-dimethyldodeca-2,8,10-trienal (compound 1-12), N-methoxy-N-methyl 2-(triphenyl-$\lambda^5$-phosphanylidene)acetamide (179 mg, 0.492 mmol) was added at room temperature, the temperature was increased to 35° C., and stirring was performed for 16 hours. The reaction mixture solution was concentrated under reduced pressure to afford a crude product. The crude product obtained was purified by thin-layer chromatography (eluent: hexane/ethyl acetate=4/1) to afford (2E,4E,6S,7S,8R,10E,12E)-7-(tert-butyldimethylsiloxy)-N-methoxy-N,6,8-trimethyltetradeca-2,4,10,12-tetraenamide (compound 1-13) (73.5 mg, 71%). At that time, 59.4 mg (10%) of compound 1-12 was collected. The physical property values of compound 1-13 are as follows.

(2E,4E,65,7S,8R,10E,12E)-7-(tert-Butyldimethylsiloxy)-N-methoxy-N,6,8-trimethyltetradeca-2,4,10,12-tetraenamide (compound 1-13)

$^1$H NMR (400 MHz, $CDCl_3$): δ 7.31 (d, J=15.6, 10.0 Hz, 1H, 3-H), 6.22-6.06 (m, 2H, H-4, H-5), 6.06-5.90 (m, 2H, H-11, H-12), 5.62-5.51 (m, 1H, H-11), 5.49-5.40 (m, 1H, H-10), 3.70 (s, 3H, NMe), 3.46 (dd, J=6.4, 3.2 Hz, 1H, H-7), 3.24 (s, 3H, OMe), 2.53-2.40 (m, 1H, H-6), 2.30-2.18 (m, 1H, H-9), 1.94-1.82 (m, 1H, H-9), 1.72 (d, J=6.4 Hz, 3H, H-14), 1.63-1.58 (m, 1H, H-8), 1.02 (d, J=6.8 Hz, 3H, 6-Me), 0.90 (s, 9H, TBS), 0.80 (d, J=6.4 Hz, 3H, 8-Me), 0.04 (s, 3H, TBS), 0.03 (s, 3H, TBS).

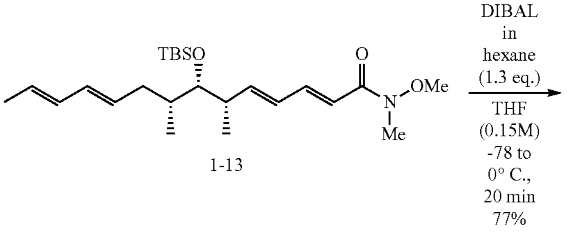

1-13

-continued

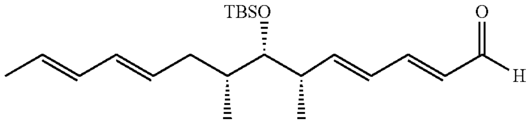

1-14

[Reduction]

To a tetrahydrofuran solution (1.7 mL) containing (2E,4E,6S,7S,8R,10E,12E)-7-(tert-butyldimethylsiloxy)-N-methoxy-N,6,8-trimethyldodeca-2,4,10,12-tetraenamide (compound 1-13) (73.5 mg, 0.174 mmol), a n-hexane solution of diisobutylaluminum hydride (1.03 M, 0.22 mL, 0.23 mmol) was added at −78° C., the temperature was increased to 0° C., and stirring was performed for 20 minutes. Methanol and saturated aqueous solution of potassium sodium tartrate were added to the reaction system at 0° C. to terminate the reaction, ethyl acetate was added to separate an organic layer, and extraction with ethyl acetate was then performed for the aqueous layer. The organic layers were combined and the resultant was dried over anhydrous sodium sulfate, and then filtered and concentrated under reduced pressure to afford a crude product. The crude product obtained was purified by thin-layer chromatography (eluent: hexane/ethyl acetate=4/1) to afford (2E,4E,6S,7S,8R,10E,12E)-7-((tert-butyldimethylsilvl)oxy)-6,8-dimethyltetradeca-2,4,10,12-tetraenal (compound 1-14) (82.8 mg, 74%). The physical property values of compound 1-14 are as follows.

(2E,4E,6S,7S,8R,10E,12E)-7-((tert-Butyldimethylsilyl)oxy)-6,8-dimethyltetradeca-2,4,10,12-tetraenal (compound 1-14)

$^1$H NMR (400 MHz, $CDCl_3$): δ 9.51 (d, J=8.4 Hz, 1H, CHO), 7.08 (dd, J=15.2, 9.6 Hz, 1H, H-3), 6.34-6.24 (m, 2H, H-4, H-6), 6.09 (dd, J=15.2, 8.4, 1H, H-2), 6.04-5.94 (m, 2H, H-11, H-12), 5.64-5.52 (m, 1H, H-13), 5.52-5.40 (m, 1H, H-10), 3.51 (dd, J=6.0, 3.2 Hz, 1H, H-7), 2.58-2.50 (m, 1H, H-6), 2.18-2.08 (m, 1H, H-9), 1.96-1.86 (m, 1H, H-9), 1.73 (d, J=6.8 Hz, 3H, H-14), 1.69-1.56 (m, 1H, H-8), 1.06 (d, J=7.2 Hz, 3H, 6-Me), 0.92 (s, 9H, TBS), 0.82 (d, J=7.6 Hz, 3H, 8-Me), 0.06 (s, 3H, TBS), 0.04 (s, 3H, TBS).

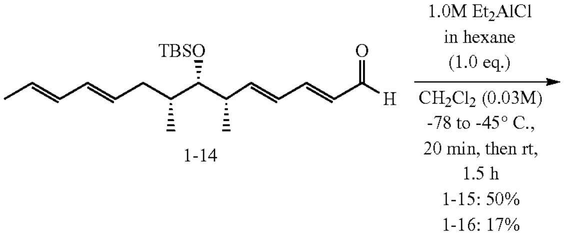

1-14

-continued

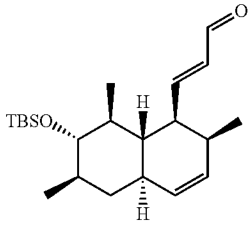

1-15

+

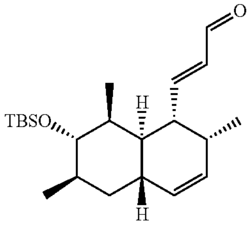

1-16

[Intramolecular Diels-Alder Reaction]

To a methylene chloride solution (2.0 mL) containing (2E,4E,6S,7S,8R,10E,12E)-7-((tert-butyldimethylsilyl)oxy)-6,8-dimethyltetradeca-2,4,10,12-tetraenal (compound 1-14) (21.2 mg, 0.0585 mmol), a n-hexane solution of diethylaluminum chloride (1.0 M, 0.06 mL, 0.06 mmol) was added at −78° C. After the temperature of the reaction system was increased to −45° C. and stirring was performed for 20 minutes, the temperature was increased to room temperature, and stirring was performed for 1.5 hours. Methanol and saturated aqueous solution of potassium sodium tartrate were added to the reaction system at 0° C. to terminate the reaction, methylene chloride was added to separate an organic layer, and extraction with methylene chloride was then performed for the aqueous layer. The organic layers were combined and the resultant was dried over anhydrous sodium sulfate, and then filtered and concentrated under reduced pressure to afford a crude product. The crude product obtained was purified by thin-layer chromatography (eluent: hexane/ethyl acetate=4/1) to afford (E)-3-((1'S,2'S,4'aR,6'R,7'S,8'S,8'aS)-7'-((tert-butyldimethylsilyl)oxy)-2',6',8'-trimethyl-1',2',4'a,5',6',7',8',8'a-octahydronaphthalen-1'-yl)lacrylaldehyde (compound 1-15) (10.5 mg, 50%), and (E)-3-((1'R,2'R,4'aS,6'R,7'S,8'S,8'aR)-7'-((tert-butyldimethylsilyl)oxy)-2',6',8'-trimethyl-1',2',4'a,5',6',7',8',8'a-octahydronaphthalen-1'-yl)acrylaidehyde (compound 1-16) (3.7 mg, 17%). The physical property values of compound 1-15 are as follows.

(E)-3-((1'S,2'S,4'aR,6'R,7'S,8'S,8'aS)-7'-((tert-butyldimethylsilyl)oxy)-2',6',8'-trimethyl-1',2',4'a,5',6',7',8',8'a-octahydronaphthalen-1'-yl)acrylaidehyde (compound 1-15)

$^1$H NMR (400 MHz, $CDCl_3$): δ 9.52 (d, J=8.0 Hz, 1H, CHO), 6.82 (dd, J=15.6, 10.8 Hz, 1H, H-3), 6.04 (dd, J=15.6, 8.0 Hz, 1H, H-2), 5.64-5.52 (m, 2H, H-3', H-4'), 2.86 (dd, J=9.6, 9.6 Hz, 1H, H-7), 2.63 (ddd, =10.4, 7.6, 6.0 Hz, 1H, H-1'), 2.38-2.22 (m, 1H, H-2'), 1.92-1.83 (m, 1H, H-4'a), 1.80 (ddd, J=13.2, 7.2, 3.6 Hz, 1H, H-5'), 1.64-1.48 (m, 3H, H-5', H-6', H-8'), 1.48-1.36 (m, 1H, 8'a-H), 0.98 (d, J=7.6 Hz, 3H, 2'-Me), 0.97 (d, J=6.4 Hz, 3H, 6'-Me), 0.97 (d, J=6.4 Hz, 3H, 8'-Me), 0.90 (s, 9H, TBS), 0.06 (s, 3H, TBS), 0.06 (s, 3H, TBS).

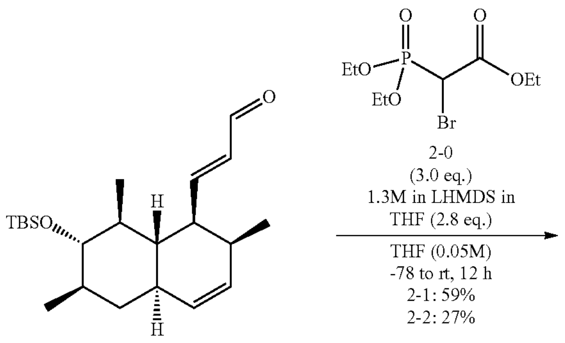

1-15

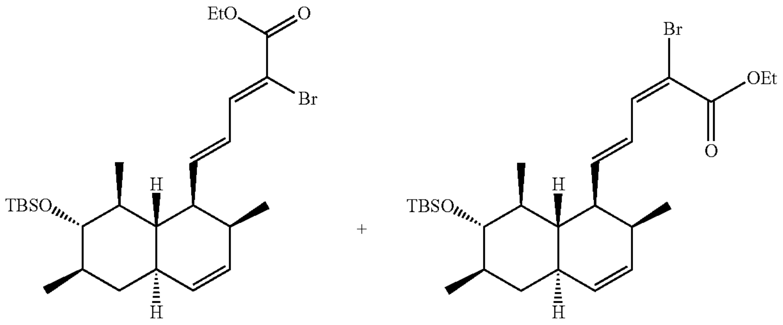

2-1 2-2

[Horner-Wadsworth-Emmons Reaction]

To a tetrahydrofuran solution (0.7 mL) containing ethyl diethylphosphonobromoacetate (compound 2-0) (26.3 mg, 0.0869 mmol), a tetrahydrofuran solution of lithium bis (trimethylsilyl)amide (1.0 M, 0.08 mL, 0.946 mmol) was added dropwise at −78° C. After the reaction mixture solution was stirred at −78° C. for 30 minutes, a tetrahydrofuran solution (0.3 mL) containing compound 1-15 (10.5 mg, 0.0290 mmol) was added, the temperature was increased to room temperature, and stirring was performed for 10 minutes. Saturated aqueous solution of ammonium chloride was added to the reaction system at 0° C. to terminate the reaction, ethyl acetate was added to separate an organic layer, and extraction with ethyl acetate was then performed for the aqueous layer. The organic layers were combined and the resultant was dried over anhydrous sodium sulfate, and then filtered and concentrated under reduced pressure to afford a crude product. The crude product obtained was purified by thin-layer chromatography (eluent: hexane/ethyl acetate=4/1) to afford ethyl (2Z,4E)-2-bromo-5-((1'S,2'S,4'aR,6'R,7'S,8'S,8'aS)-7'-((tert-butyldimethylsilyl)oxy)-2',6',8'-trimethyl-1',2',4'a,5',6',7',8',8'a-octahydronaphthalen-1'-yl)penta-2,4-dienoate (compound 2-1) (8.8 mg, two-step yield: 59%), and ethyl (2E,4E)-2-bromo-5-((1'S,2'S,4'aR,6'R,7'S,8'S,8'aS)-7'-((tert-butyldimethylsilyl)oxy)-2',6',8'-trimethyl-1',2',4'a,5',6',7',8',8'a-octahydronaphthalen-1'-yl)penta-2,4-dienoate (compound 2-2) (4.0 mg, two-step yield: 27%). The physical property values of compound 2-1 are as follows.

Ethyl (2Z,4E)-2-bromo-5-((1'S,2'S,4'aR,6'R,7'S,8'S,8'aS)-7'-((tert-butyldimethylsilyl)oxy)-2',6',8'-trimethyl-1',2',4'a,5',6',7',8',8'a-octahydronaphthalen-1'-yl)penta-2,4-dienoate (compound 2-1)

$^1$H NMR (500 MHz, $CDCl_3$): δ 7.65 (d, J=9.0 Hz, 1H, H-3), 6.47-6.30 (m, 2H, H-4, H-5), 5.58 (ddd, J=9.5, 3.0, 2.5 Hz, 1H, H-4'), 5.49 (ddd, J=9.5, 2.0, 2.0 Hz, 1H, H-3'), 4.29 (q, J=7.5 Hz, 2H, OEt), 2.86 (dd, J=9.5, 9.5 Hz, 1H, H-7'), 2.54 (ddd, J=9.0, 9.0, 5.0 Hz, 1H, H-1'), 2.30-2.18 (m, 1H, H-2'), 1.91-1.82 (m, 1H, H-4'a), 1.76 (ddd, J=13.0, 3.5, 3.5 Hz, 1H, H-5'), 1.60-1.49 (m, 3H, H-5', H-6', H-8'), 1.46-1.36 (m, 1H, H-8'a), 1.35 (t, J=7.5 Hz, 3H, OEt), 1.00 (d, J=6.5 Hz, 3H, 2'-Me), 0.98 (d, J=7.0 Hz, 3H, 8'-Me), 0.96 (d, J=6.5 Hz, 3H, 6'-Me), 0.91 (s, 9H, TBS), 0.07 (s, 6H, TBS).

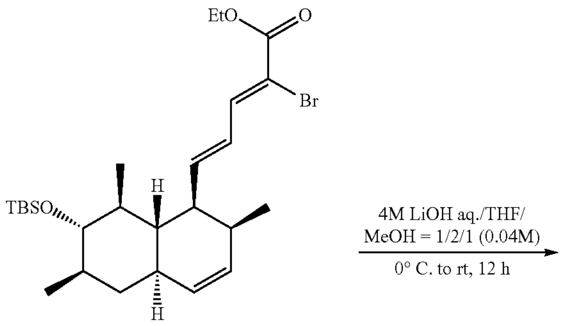

2-1

-continued

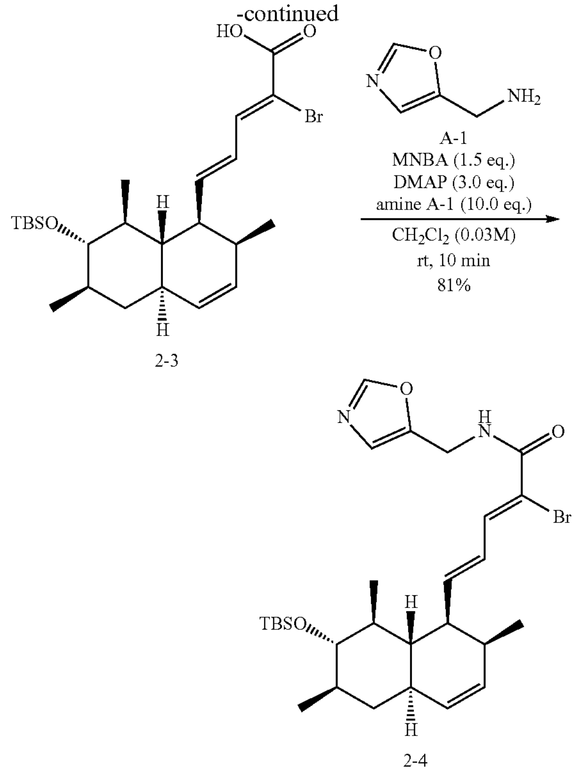

2-3

2-4

[Hydrolysis]

To a mixed solution containing ethyl (2Z,4E)-2-bromo-5-((1'S,2'S,4'aR,6'R,7'S,8'S,8'aS)-7'-((tert-butyldimethylsilyl)oxy)-2',6',8'-trimethyl-1',2',4'a,5',6',7',8',8'a-octahydronaphthalen-1'-yl)penta-2,4-dienoate (compound 2-1) (84.7 mg, 0.166 mmol) in methanol (1.0 mL) and tetrahydrofuran (2.0 mL), 4.0 M aqueous solution of lithium hydroxide (1.0 mL, 4.00 mmol) was added at 0° C., the temperature was increased to room temperature, and stirring was performed for 12 hours. To the reaction system, 1.0 M hydrochloric acid was added at 0° C. to terminate the reaction, ethyl acetate was added to separate an organic layer, and extraction with ethyl acetate was then performed for the aqueous layer. The organic layers were combined and the resultant was dried over anhydrous sodium sulfate, and then filtered and concentrated under reduced pressure to afford a crude product of compound 2-3. This crude product was directly used for the subsequent reaction without purification.

[Amidation]

To a methylene chloride solution (5.5 mL) containing the crude product of compound 2-3, 2-methyl-6-nitrobenzoic anhydride (85.5 mg, 0.248 mmol) and 4-dimethylaminopyridine (60.7 mg, 0.497 mmol) were added at room temperature. After the reaction mixture solution was stirred for 10 minutes, 5-aminomethyl-1,3-oxazole (amine A-1) (162.4 mg, 1.66 mmol) was added, and stirring was performed at room temperature for 10 minutes. Saturated aqueous solution of ammonium chloride was added to the reaction system at 0° C. to terminate the reaction, methylene chloride was added to separate an organic layer, and extraction with methylene chloride was then performed for the aqueous layer. The organic layers were combined and the resultant was dried over anhydrous sodium sulfate, and then filtered and concentrated under reduced pressure to afford a crude product. The crude product obtained was purified by thin-layer chromatography (eluent: chloroform/methanol=20/1) to afford (2Z,4E)-2-bromo-5-((1'S,2'S,4'aR,6'R,7'S,8'S,8'aS)-7'-((tert-butyldimethylsilyi)oxy)-2',6',8'-trimethyl-(oxazol-5"-ylmethyl)penta-2,4-dienamide (compound 2-4) (75.6 mg, two-step yield: 81%). The physical property values of compound 2-1 are as follows.

(2Z,45)-2-Bromo-5-((1',2'S,4'aR,6'R,7'S,8'S,8'aS)-7'-((tert-butyldimethylsilyl)oxy)-2',6',8'-trimethyl-(oxazol-5"-ylmethyl)penta-2,4-dienamide (compound 2-4)

$^1H$ NMR (500 MHz, $CDCl_3$): δ 7.85 (s, 1H, H-2"), 7.77 (d, J=10.5 Hz, 1H, H-3), 7.04 (s, 1H, H-4"), 6.94 (brt, J=5.5 Hz, 1H, NH), 6.36 (dd, J=15.0, 10.5 Hz, 1H, H-4), 6.28 (dd, J=15.0, 10.0 Hz, 1H, H-5), 5.57 (ddd, J=9.5, 4.0, 3.0 Hz, 1H, H-4'), 5.47 (ddd, J=9.5, 2.0, 2.0 Hz, 1H, H-3'), 4.60 (d, J=5.5 Hz, 2H, $CH_2Ar$), 2.85 (dd, J=9.5, 9.5 Hz, 1H, H-7'), 2.51 (ddd, J=10.0, 8.5, 6.0 Hz, 1H, H-1'), 2.27-2.17 (m, 1H, H-2'), 1.91-1.78 (m, 1H, H-4'a), 1.88-1.71 (m, 2H, H-6', H-8'), 1.58-1.47 (m, 1H, H-5'), 1.44-1.30 (m, 1H, H-8'a), 0.98 (d, J=7.0 Hz, 3H, 2'-Me), 0.97 (d, J=7.0 Hz, 3H, 8'-Me), 0.94 (d, J=6.5 Hz, 3H, 6'-Me), 0.89 (s, 9H, TBS), 0.06 (s, 6H, TBS).

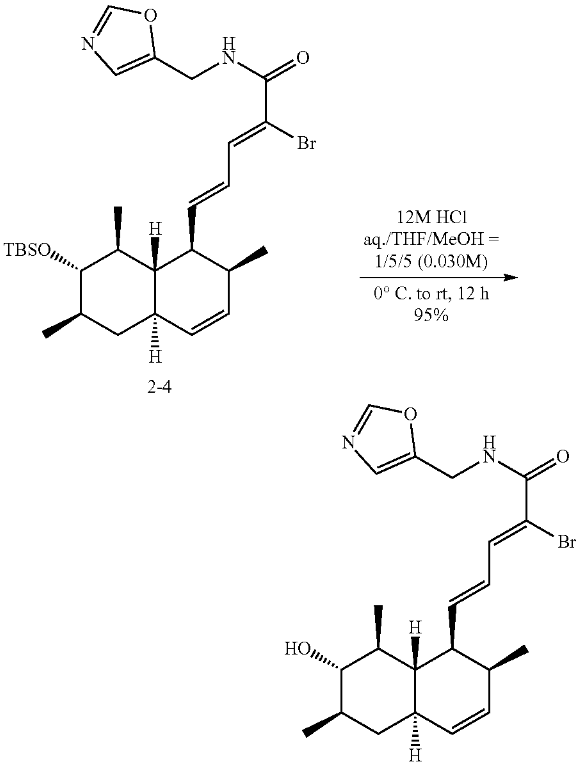

2-4

RS1

[Deprotection]

To a mixed solution containing (2Z,4E)-2-bromo-5-((1'S,2'S,4'aR,6'R,7'S,8'S,8'aS)-7'-((tert-butyldimethylsilyl)oxy)-2',6',8'-trimethyl-1',2',4'a,5',6',7',8',8'a-octahydronaphthalen-1'-yl)-N-(oxazol-5"-ylmethyl)penta-2,4-dienamide (compound 2-4) (75.6 mg, 0.134 mmol) in methanol (2.0 mL) and tetrahydrofuran (2.0 mL), 12 M hydrochloric acid (0.40 mL, 4.80 mmol) was added at 0° C., the temperature was increased to room temperature, and stirring was performed for 12 hours. Saturated aqueous solution of sodium hydrogen carbonate was added to the reaction system at 0° C. to terminate the reaction, ethyl acetate was added to separate an organic layer, and extraction with ethyl acetate was then performed for the aqueous layer. The organic layers were combined and the resultant was dried over anhydrous sodium sulfate, and then filtered and concentrated under reduced pressure to afford a crude product. The crude product obtained was purified by thin-layer (2Z,4E)-2-bromo-5-5((1'S,2'S,4'aR,6'R,7'S,8'S,8'aS)-7'-hydroxy-2',6',8'-trimethyl-1',2',4'a,5',6',7',8',8'a-octahydronaphthalen-1'-yl)-N-(oxazol-5"-ylmethyl)penta-2,4-dienamide (compound RS1) (57.3 mg, 95%). The physical property values of compound RS1 are as follows.

(2Z,4E)-2-Bromo-5-((1'S,2'S,4'aR,6'R,7'S,8'S,8'aS)-7'-hydroxy-2',6',8'-trimethyl-1',2',4'a,5',6',7',8',8'a-octahydronaphthalen-1'-yl)-N-(oxazol-5"-ylmethyl) penta-2,4-dienamide (compound RS1)

$^1$H NMR (500 MHz, $CDCl_3$): δ 7.85 (s, 1H, H-2"), 7.78 (d, J=10.5 Hz, 1H, H-3), 7.04 (s, 1H, H-4"), 6.95 (brt, J=5.5 Hz, 1H, NH), 6.41 (dd, J=15.0, 10.5 Hz, 1H, H-4), 6.30 (dd, J=15.0, 10.0 Hz, 1H, H-5), 5.58 (ddd, J=9.5, 4.0, 3.0 Hz, 1H, H-4'), 5.45 (ddd, J=9.5, 2.0, 2.0 Hz, 1H, H-3'), 4.61 (d, J=5.5 Hz, 2H, $CH_2$Ar), 2.73 (dd, J=9.5, 9.5 Hz, 1H, H-7'), 2.54 (ddd, J=10.0, 10.0, 5.0 Hz, 1H, H-1'), 2.27-2.17 (m, 1H, H-2'), 1.92-1.82 (m, 1H, H-4'a), 1.80-1.71 (m, 2H, H-5'), 1.76-1.64 (m, 2H, H-6', H-8'), 1.54-1.44 (m, 1H, H-5'), 1.36-1.22 (m, 1H, H-8'a), 1.07 (d, J=6.5 Hz, 3H, 2'-Me), 1.04 (d, J=7.0 Hz, 3H, 8'-Me), 0.95 (d, J=6.5 Hz, 3H, 6'-Me).

Synthesis Example 2: Synthesis of (2Z,4E)-2-bromo-5-((1'S,2'S,4'aR,6'R,7'S,8'S,8'aS)-7'-hydroxy-2',6'8'-trimethyl-1',2',4'a,5',6',7',8',8'a-octahydronaphthalen-1'-yl)-N-(thiazol-5"-ylmethyl)penta-2,4-dienamide (compound RS2)

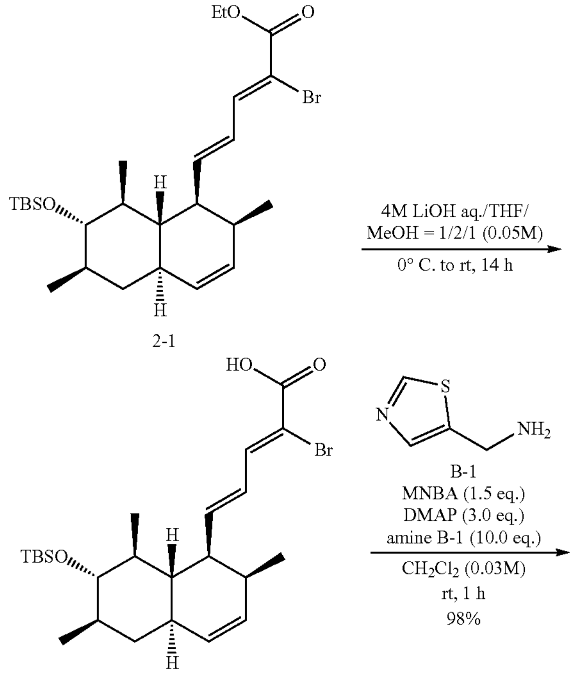

2-1

2-3

-continued

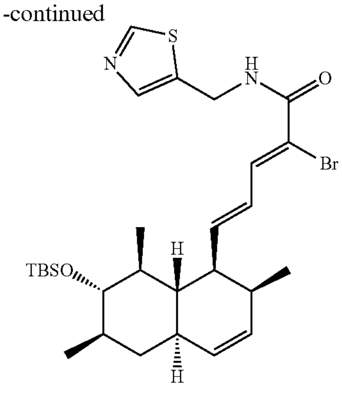

2-5

[Hydrolysis]

To a mixed solution containing ethyl (2Z,4E)-2-bromo-5-((1'S,2'S,4'aR,6'R,7'S,8'S,8'aS)-7'-((tert-butyldimethylsilyl)oxy)-2',6',8'-trimethyl-1',2',4'a,5',6',7',8',8'a-octahydronaphthalen-1'-yl)penta-2,4-dienoate (compound 2-1) (45.7 mg, 0.089 mmol) in methanol (0.45 mL) and tetrahydrofuran (0.90 mL), 4.0 M aqueous solution of lithium hydroxide (0.45 mL, 1.80 mmol) was added at 0° C., the temperature was increased to room temperature, and stirring was performed for 14 hours. To the reaction system, 1.0 M hydrochloric acid was added at 0° C. to terminate the reaction, ethyl acetate was added to separate an organic layer, and extraction with ethyl acetate was then performed for the aqueous layer. The organic layers were combined and the resultant was dried over anhydrous sodium sulfate, and then filtered and concentrated under reduced pressure to afford a crude product of compound 2-3. This crude product was directly used for the subsequent reaction without purification.

[Amidation]

To a methylene chloride solution (3.0 mL) containing the crude product of compound 2-3, 2-methyl-6-nitrobenzoic anhydride (46.1 mg, 0.134 mmol) and 4-dimethylaminopyridine (32.7 mg, 0.268 mmol) were added at room temperature. After the reaction mixture solution was stirred for 10 minutes, 5-aminomethyl-1,3-thiazole (amine B-1) (102.0 mg, 0.893 mmol) was added, and stirring was performed at room temperature for 1 hour. Saturated aqueous solution of ammonium chloride was added to the reaction system at 0° C. to terminate the reaction, methylene chloride was added to separate an organic layer, and extraction with methylene chloride was then performed for the aqueous layer. The organic layers were combined and the resultant was dried over anhydrous sodium sulfate, and then filtered and concentrated under reduced pressure to afford a crude product. The crude product obtained was purified by thin-layer chromatography (eluent: chloroform/methanol=20/1) to afford (2Z,4E)-2-bromo-5-((1'S,2'S,4'aR,6'R,7'S,8'S,8'aS)-7'-((tert-butyldimethylsilyl)oxy)-2',6',8'-trimethyl-(thiazol)-1',2',4'a,5',6',7',8',8'a-octahydronaphthalen-1'-yl)-N-thiazol-5"-ylmethyl)penta-2,4-dienamide (compound 2-5) (50.6 mg, two-step yield: 98%). The physical property values of compound 2-5 are as follows.

(2Z,4E)-2-Bromo-5-((1'S,2'S,4'aR,6'R,7'S,8'S,8'aS)-7'-((tert-butyldimethylsilyl)oxy)-1',2',4'a,5',6',7',8',8'a-octahydronaphthalen-1'-yl)-N-(thiazol-5"-ylmethyl)penta-2,4-dienamide (compound 2-5)

$^1$H NMR (500 MHz, $CDCl_3$): δ 8.80 (s, 1H, H-2"), 7.84 (s, 1H, H-4"), 7.78 (d, J=10.5 Hz, 1H, H-3), 7.05 (ort, J=5.5

Hz, 1H, NH), 6.38 (dd, J=15.0, 10.5 Hz, 1H, H-4), 6.28 (dd, J=15.0, 10.0 Hz, 1H, H-5), 5.60-5.54 (m, 1H, H-4'), 5.50-5.45 (m, 1H, H-3'), 4.75 (d, J=5.5 Hz, 2H, $CH_2Ar$), 2.86 (dd, J=9.0, 9.0 Hz, 1H, H-7'), 2.52 (ddd, J=10.0, 10.0, 5.5 Hz, 1H, H-1'), 2.27-2.18 (m, 1H, H-2'), 1.92-1.60 (m, 4H, H-4'a, H-5', H-6', H-8'), 1.60-1.44 (m, 1H, H-5'), 1.44-1.34 (m, 1H, H-8'a), 0.98 (d, J=6.0 Hz, 3H, 2'-Me), 0.97 (d, J=6.0 Hz, 3H, 8'-Me), 0.96 (d, J=7.0 Hz, 3H, 6'-Me), 0.90 (s, 9H, TBS), 0.07 (s, 6H, TBS).

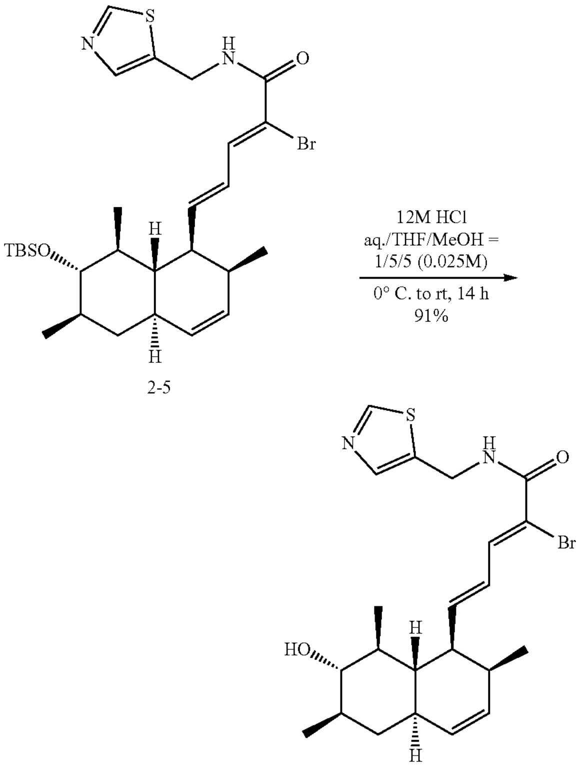

2-5

RS2

[Deprotection]

To a mixed solution containing (2Z,4E)-2-bromo-5-((1'S, 2'S,4'aR,6'R,7'S,8'S,8'S)-7'-((tert-butyldimethylsilyl)oxy)-2',6',8'-trimethyl-1',2',4'a,5',6',7',8',8'a-octahydronaphthalen-1'-yl)-N-(thiazol-5"-ylmethyl)penta-2,4-dienamide (compound 2-5) (50.6 mg, 0.087 mmol) in methanol (1.6 mL) and tetrahydrofuran (1.6 mL), 12 M hydrochloric acid (0.32 mL, 3.84 mmol) was added at 0° C., the temperature was increased to room temperature, and stirring was performed for 14 hours. Saturated aqueous solution of sodium hydrogen carbonate was added to the reaction system at 0° C. to terminate the reaction, ethyl acetate was added to separate an organic layer, and extraction with ethyl acetate was then performed for the aqueous layer. The organic layers were combined and the resultant was dried over anhydrous sodium sulfate, and then filtered and concentrated under reduced pressure to afford a crude product. The crude product obtained was purified by thin-layer (2Z,4E)-2-bromo-5-((1'S,2'S,4'aR,6'R,7'S,8'S,8'aS)-7'-hydroxy-2',6',8'-trimethyl-1',2',4'a,5',6',7',8',8'a-octahydronaphthalen-1'-yl)-N-(thiazol-5"-ylmethyl)penta-2,4-dienamide (compound RS2) (37.0 mg, 91%). The physical property values of compound RS2 are as follows.

(2Z,4E)-2-Bromo-5-((1'S,2'S,4'aR,6'R,7'S,8'S,8'aS)-7'-hydroxy-2',6',8'-trimethyl-1',2',4'a,5',6',7',8',8'a-octahydronaphthalen-1'-yl)-N-(thiazol-5"-ylmethyl) penta-2,4-dienamide (compound RS2)

$^1$H NMR (500 MHz, $CDCl_3$): δ 8.92 (s, 1H, H-2"), 7.91 (s, 1H, H-4"), 7.80 (d, J=10.5 Hz, 1H, H-3), 7.14-7.11 (brm, 1H, NH), 6.44 (dd, J=15.5, 10.5 Hz, 1H, H-4), 6.31 (dd, J=15.0, 10.0 Hz, 1H, H-5), 5.61-5.55 (m, 1H, H-4'), 5.48-5.42 (m, 1H, H-3'), 4.76 (d, J=6.0 Hz, 2H, $CH_2Ar$), 2.74 (dd, J=10.0, 10.0 Hz, 1H, H-7'), 2.55 (ddd, J=10.0, 10.0, 5.5 Hz, 1H, H-1'), 2.30-2.17 (m, 1H, H-2'), 1.97-1.70 (m, 4H, H-4'a, H-5', H-6', H-8'), 1.56-1.43 (m, 1H, H-5'), 1.37-1.28 (m, 1H, H-8'a), 1.07 (d, J=6.0 Hz, 3H, 2'-Me), 1.05 (d, J=6.0 Hz, 3H, 8'-Me), 0.96 (d, J=7.0 Hz, 3H, 6'-Me).

Synthesis Example 3: Synthesis of (2Z,4E)-2-bromo-5-((1'S,2'S,4'aR,6'R,7'S,8'S,8'aS)-7'-hydroxy-2',6',8'-trimethyl-1',2',4'a,5',6',7',8',8'a-octahydronaphthalen-1'-yl)-N-(oxazol-4"-ylmethyl)penta-2,4-dienamide (compound RS3)

Compound RS3 was synthesized in the same manner as in Synthesis Example 1, except that, in amidation of compound 2-3, 4-aminomethyl-1,3-oxazole was used in place of 5-aminomethyl-1,3-oxazole. The physical property values of compound RS3 are as follows.

RS3

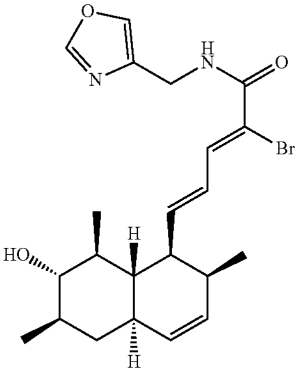

(2Z,4E)-2-Bromo-5-((1'S,2'S,4'aR,6'R,7'S,8'S,8'aS)-7'-hydroxy-2',6',8'-trimethyl-1',2',4'a,5',6',7',8',8'a-octahydronaphthalen-1'-yl)-N-(oxazol-4"-ylmethyl) penta-2,4-dienamide (compound RS3)

$^1$NMR (500 MHz, $CDCl_3$): δ 7.87 (s, 1H, H-2"), 7.75 (s, 1H, H-3), 7.65 (s, 1H, H-5"), 7.18-7.09 (brm, 1H, NH), 6.44-6.25 (m, 2H, H-4, H-5), 5.62-5.53 (m, 1H, H-3'), 4.47 (d, J=5.0 Hz, 2H, $CH_2Ar$), 2.78-2.68 (m, 1H, H-7'), 2.53 (ddd, J=9.5, 9.5, 5.0 Hz, 1H, H-1'), 2.28-2.16 (m, 1H, H-2'), 1.94-1.82 (m, 1H, H-6'), 1.80-1.71 (m, 1H, H-5'), 1.71-1.56 (m, 1H, H-8'), 1.56-1.42 (m, 1H, H-5'), 1.38-1.22 (m, 1H, H-8'a), 1.06 (d, J=6.0 Hz, 3H, 2'-Me), 1.04 (d, J=6.0 Hz, 3H, 8'-Me), 0.95 (d, J=7.0 Hz, 3H, 6'-Me).

Synthesis Example 4: Synthesis of (2Z,4E)-2-bromo-5-((1'S,2'S,4'aR,6'R,7'S,8'S,8'aS)-7'-hydroxy-2',6',8'-trimethyl-1',2',4'a,5',6',7',8',8'a-octahydronaphthalen-1'-yl)-N-(thiazol-2"-ylmethyl)penta-2,4-dienamide (compound RS4)

Compound RS4 was synthesized in the same manner as in Synthesis Example 1, except that, in amidation of compound 2-3, 2-aminomethyl-1,3-thiazole was used in place of 5-aminomethyl-1,3-oxazole. The physical property values of compound RS4 are as follows.

RS4

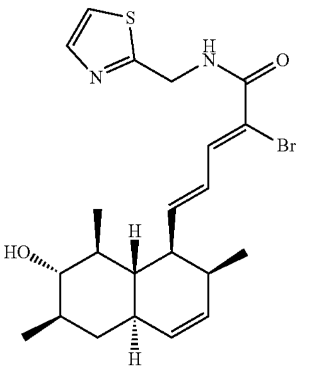

(2Z,4E)-2-Bromo-5-((1'S,2'S,4'aR,6'R,7'S,8'S,8'aS)-7'-hydroxy-2',6',8'-trimethyl-1',2',4'a,5',6',7',8',8'a-octahydronaphthalen-1'-yl)-N-(thiazol-2"-ylmethyl) penta-2,4-dienamide (compound RS4)

$^1$H NMR (400 MHz, $CD_3OD$): δ 7.72 (s, 1H, H-4"), 7.63 (s, 1H, H-3), 7.52 (d, J=3.2 Hz, 1H, H-5"), 6.54-6.36 (m, 2H, H-4, H-5), 5.61 (ddd, J=9.2, 4.4, 2.8 Hz, 1H, H-4'), 5.49 (ddd, J=9.2, 1.6, 1.6 Hz, 1H, H-3'), 4.77 (s, 2H, $CH_2$Ar), 2.63 (dd, J=9.6, 9.6 Hz, 1H, H-7'), 2.57 (ddd, J=8.4, 8.4, 2.8 Hz, 1H, H-1'), 2.30-2.14 (m, 1H, H-2'), 1.95-1.82 (m, 1H, H-4'a), 1.77 (ddd, J=13.2, 3.6, 3.6 Hz, 1H, H-5'), 1.54-1.40 (m, 1H, H-6'), 1.37-1.21 (m, 3H, H-5', H-8', H-8'a), 1.08 (d, J=6.4 Hz, 3H, 2'-Me), 1.03 (d, J=6.0 Hz, 3H, 8'-Me), 0.99 (d, J=7.2 Hz, 3H, 6'-Me).

Synthesis Example 5: Synthesis of (2Z,4E)-2-bromo-5-((1'S,2'S,4'aR,6'R,7'S,8'S,8'aS)-7'-hydroxy-2',6',8'-trimethyl-1',2',4'a,5',6',7',8',8'a-octahydronaphthalen-1'-yl)-N-(pyridin-3"-ylmethyl)penta-2,4-dienamide (compound RS5)

Compound RS5 was synthesized in the same manner as in Synthesis Example 1, except that, in amidation of compound 2-3, 3-aminomethylpyridine was used in place of 5-aminomethyl-1,3-oxazole. The physical property values of compound RS5 are as follows.

RS5

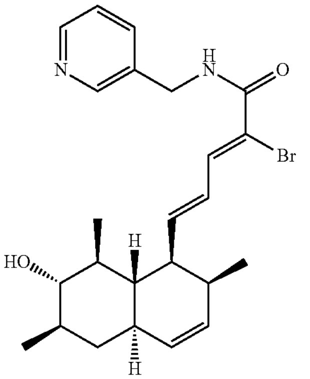

(2Z,4E)-2-Bromo-5-((1'S,2'S,4'aR,6'R,7'S,8'S,8'aS)-7'-hydroxy-2',6',8'-trimethyl-1',2',4'a,5',6',7',8',8'a-octahydronaphthalen-1'-yl)-N-(pyridin-3"-ylmethyl) penta-2,4-dienamide (compound RS5)

$^1$H NMR (500 MHz, $C_6D_6$): δ 8.40 (s, 1H, H-2"), 8.37 (d, J=3.0 Hz, 1H, H-6"), 8.08 (d, J=11.0 Hz, 1H, H-3), 7.16-7.09 (m, 1H, H-4"), 6.59 (dd, J=7.5, 4.5 Hz, 1H, H-5"), 6.46 (brt, J=6.5 Hz, 1H, NH), 6.37 (dd, J=15.5, 10.5 Hz, 1H, H-4), 6.05 (dd, J=15.5, 10.0 Hz, 1H, H-5), 5.44 (ddd, J=9.5, 4.0, 3.0 Hz, 1H, H-4'), 5.33 (ddd, J=9.5, 2.0, 2, 0 Hz, 1H, H-3'), 3.96 (d, J=5.5 Hz, 2H, $CH_2$Ar), 2.35 (dd, J=10.0, 10.0 Hz, 1H, H-7'), 2.22 (ddd, J=9.5, 9.5, 5.5 Hz, 1H, H-1'), 2.00-1.90 (m, 1H, H-2'), 1.59-1.51 (m, 1H, H-4'a), 1.43 (ddd, J=13.0, 3.5, 3.5 Hz, 1H, H-5'), 1.39-1.19 (m, 2H, H-6', H-8'), 1.24-1.12 (m, 1H, H-5'), 1.04-0.88 (m, 1H, H-8'a), 0.92 (d, J=6.5 Hz, 3H, 2'-Me), 0.91 (d, J=6.5 Hz, 3H, 8'-Me), 0.73 (d, J=7.5 Hz, 3H, 6'-Me).

Synthesis Example 6: Synthesis of (2Z,4E)-2-bromo-5-((1'S,2'S,4'aR,7'S,8'S,8'aS)-7'-hydroxy-2',8'-dimethyl-1',2',4'a,5',6',7',8',8'a-octahydronaphthalen-1'-yl)-N-(thiazol-5"-ylmethyl)penta-2,4-dienamide (compound RS6)

Compound RS6 was synthesized in the same manner as in Synthesis Example 2, in oxidation and Mukaiyama Aldol reaction with an Evans asymmetric auxiliary group, (4E, 6E)-octa-4,6-dien-1-ol was used in place of compound 1-5. The physical property values of compound RS6 are as follows.

RS6

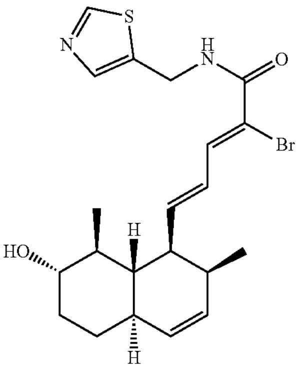

(2Z,4E)-2-Bromo-5-((1'S,2'S,4'aR,7'S,8'S,8'aS)-7'-hydroxy-2',8'-dimethyl-1',2',4'a,5',6',7',8',8'a-octahydronaphthalen-1'-yl)-N-(thiazol-5"-ylmethyl)penta-2,4-dienamide (compound RS6)

$^1$H NMR (300 MHz, $CD_3OD$): δ 8.89 (s, 1H, H-2"), 7.79 (d, J=3.0 Hz, 1H, H-4"), 7.59 (d, J=9.6 Hz, 1H, H-3), 6.53-6.30 (m, 2H, H-4, H-5), 5.60 (ddd, J=9.3, 3.6, 3.0 Hz, 1H, H-4'), 5.48 (ddd, J=9.3, 1.8, 1.8 Hz, 1H, H-3'), 4.67 (s, 2H, $CH_2$Ar), 3.08 (ddd, J=10.8, 10.8, 4.5 Hz, 1H, H-7'), 2.56 (ddd, J=9.3, 9.3, 5.4 Hz, 1H, H-1'), 2.30-2.12 (m, 1H, H-2'), 2.04-1.90 (m, 1H, H-4'a), 1.90-1.70 (m, 1H, H-5'), 1.48-1.27 (m, 1H, H-8'), 1.37-1.12 (m, 2H, H-6', H-8'a), 1.15-1.10 (m, 1H, H-6'), 1.06 (d, J=6.3 Hz, 3H, 2'-Me), 0.97 (d, J=7.2 Hz, 3H, 8'-Me).

Synthesis Example 7: Synthesis of (2Z,4E)-2-bromo-5-((1'S,2'S,4'aR,7'S,8'S,8'aS)-7'-hydroxy-2',8'-dimethvl-1',2',4'a,5',6',7',8',8'a-octahydronaphthalen-1'-yl)-N-(pyridin-3"-ylmethyl)penta-2,4-dienamide (compound RS7)

Compound RS7 was synthesized in the same manner as in Synthesis Example 5, in oxidation and Mukaiyama Aldol reaction with an Evans asymmetric auxiliary group, (4E, 6E)-octa-4,6-dien-1-ol was used in place of compound 1-5. The physical property values of compound RS7 are as follows.

RS7

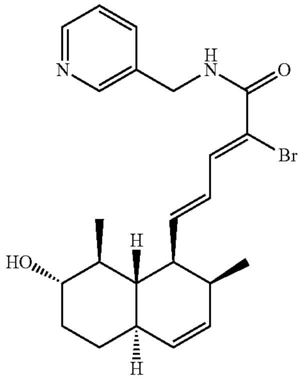

(2Z,4E)-2-Bromo-5-((1'S,2'S,4'aR,7'S,8'S,8'aS)-7'-hydroxy-2',8'-dimethyl-1',2',4'a,5',6',7',8',8'a-octahydronaphthalen-1'-yl)-N-(pyridin-3"-ylmethyl)penta-2,4-dienamide (compound RS7)

$^1$H NMR (500 MHz, $CD_3OD$): δ 8.50 (s, 1H, H-2"), 8.42 (d, J=4.5 Hz, 1H, H-6"), 7.81-7.74 (m, 1H, H-4"), 7.59 (d, J=9.5 Hz, 1H, H-3), 7.40 (dd, J=7.5, 4.5 Hz, 1H, H-5"), 6.49-6.35 (m, 2H, H-4, H-5), 5.60 (ddd, J=9.0, 4.0, 2.5 Hz, 1H, H-4'), 5.49 (ddd, J=9.0, 3.0, 3.0 Hz, 1H, H-3'), 4.50 (s, 2H, $CH_2Ar$), 3.07 (ddd, J=11.0, 11.0, 5.0 Hz, 1H, H-7'), 2.70-2.16 (m, 1H, H-2'), 2.05-1.93 (m, 1H, H-4'a), 1.86-1.75 (m, 1H, H-5'), 1.45-1.31 (m, 1H, H-8'), 1.37-1.19 (m, 2H, H-6', H-8'a), 1.26-1.14 (m, 1H, H-6'), 1.06 (d, J=6.0 Hz, 3H, 2'-Me), 0.97 (d, J=7.0 Hz, 3H, S'-Me).

Synthesis Example 8: Synthesis of (2Z,4E)-2-bromo-5-((1'S,2'S,4'aR,6'R,7'S,8'S,8'aS)-7'-hydroxy-2',6',8'-trimethyl-1',2',4'a,5',6',7',8',8'a-octahydronaphthalen-1'-yl)-N-(pyridin-2"-ylmethyl)penta-2,4-dienamide (compound RS8)

Compound RS8 was synthesized in the same manner as in Synthesis Example 1, except that, in amidation of compound 2-3, 2-aminomethylpyridine was used in place of 5-aminomethyl-1,3-oxazole. The physical property values of compound RS8 are as follows.

RS8

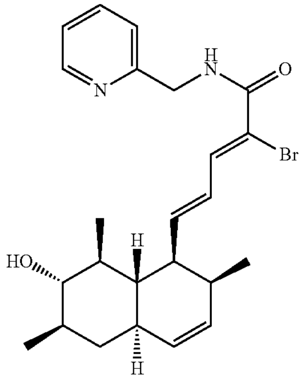

(2Z,4E)-2-Bromo-5-((1'S,2'S,4'aR,6'R,7'S,8'S,8'aS)-7'-hydroxy-2',6',8'-trimethyl-1',2',4'a,5',6',7',8',8'a-octahydronaphthalen-1'-yl)-N-(pyridin-2"-ylmethyl)penta-2,4-dienamide (compound RS8)

$^1$H NMR (400 MHz, acetone-$d_6$): δ 8.56-8.50 (m, 1H, H-6"), 8.23 (brt, J=5.2 Hz, 1H, NH), 7.76 (ddd, J=7.6, 7.6, 1.6 Hz, 1H, H-4"), 7.75 (d, J=10.8 Hz, 1H, H-3), 7.38-7.33 (m, 1H, H-3"), 7.29-7.23 (m, 1H, H-5"), 6.56 (dd, J=15.2, 10.4 Hz, 1H, H-4), 6.41 (dd, J=15.2, 10.4 Hz, 1H, H-5), 5.61 (ddd, J=9.2, 4.4, 2.8 Hz, 1H, H-4'), 5.48 (ddd, J=9.2, 2.0, 2.0 Hz, 1H, H-5'), 4.60 (d, J=5.2 Hz, 2H, $CH_2Ar$), 3.50 (d, J=6.8 Hz, 1H, H-7'), 2.67-2.57 (m, 1H, H-8'), 2.60 (ddd, J=10.4, 9.2, 5.2 Hz, 1H, H-I'), 2.30-2.18 (m, 1H, H-2'), 1.96-1.84 (m, 1H, H-4'a), 1.74 (ddd, J=13.2, 3.6, 3.6 Hz, 1H, H-5'), 1.54-1.39 (m, 1H, H-5'), 1.38-1.25 (m, 1H, H-8'a), 1.11 (d, J=6.0 Hz, 3H, 8'-Me), 1.02 (d, J=6.0 Hz, 3H, 2'-Me), 1.00 (d, J=7.6 Hz, 3H, 6'-Me).

HRMS (EST): m/z calcd for $C_{24}H_{31}BrN_2O_2Na$ 481.1461 $[M+Na]^+$; found 481.1444.

Synthesis Example 9: Synthesis of pyridin-3"-ylmethyl (2Z,4E)-2-bromo-5-((1'S,2'S,4'aR,6'R,7'S,8'S,8'aS)-7'-hydroxy-2',6',8'-trimethyl-1',2',4'a,5',6',7',8',8'a-octahydronaphthalen-1'-yl)penta-2,4-diencate (compound RS9)

Compound RS9 was synthesized in the same manner as in Synthesis Example 1, except that, in dehydration condensation reaction of compound 2-3, 3-pyridinemethanol was used in place of 5-aminomethyl-1,3-oxazole. The physical property values of compound RS9 are as follows.

RS9

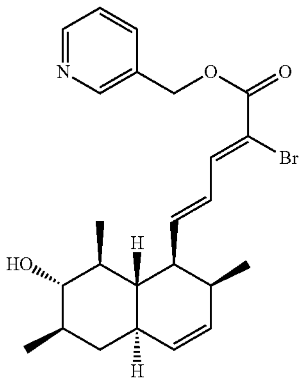

Pyridin-3"-ylmethyl (2Z,4E)-2-bromo-5-((1'S,2'S,4'aR,6'R,7'S,8'S,8'aS)7'-hydroxy-2',6',8'-trimethyl-1',2',4'a,5',6',7',8',8'a-octahydronaphthalen-1'-yl)penta-2,4-dienoate (compound RS9)

$^1$H NMR (500 MHz, acetone-$d_6$): δ 8.69 (s, 1H, H-2"), 8.57 (d, J=3.5 Hz, 1H, H-6"), 7.88-7.85 (m, 1H, H-4"), 7.85 (d, J=10.5 Hz, 1H, H-3), 7.43-7.38 (m, 1H, H-5"), 6.68 (dd, J=15.0, 10.5 Hz, 1H, H-4), 6.46 (dd, J=15.0, 10.0 Hz, 1H, H-5), 5.60 (ddd, J=9.0, 3.0, 3.0 Hz, 1H, H-4'), 5.48 (ddd, J=9.0, 2.5, 1.5 Hz, 1H, H-3'), 5.33 (s, 2H, $CH_2$Ar), 3.49 (d, J=7.0 Hz, 1H, H-7'), 2.66-2.56 (m, 2H, H-8', H-1'), 2.30-2.14 (m, 1H, H-2'), 1.94-1.84 (m, 1H, H-4'a), 1.75 (ddd, J=13.0, 3.0, 3.0 Hz, 1H, H-5'), 1.55-1.40 (m, 1H, H-5'), 1.39-1.25 (m, 1H, H-8'a), 1.08 (d, J=6.0 Hz, 3H, 8'-Me), 1.01 (d, J=6.0 Hz, 3H, 2'-Me), 0.97 (d, J=7.5 Hz, 3H, 6'-Me).

HRMS (ESI): m/z calcd for $C_{24}H_{31}BrNO_3$ 460.1482 $[M+H]^+$; found 460.1483.

Synthesis Example 10: Synthesis of pyridin-2"-ylmethyl (2Z,4E)-2-bromo-5-((1'S,2'S,4'aR,6'R,7'S,8'S,8'aS)-7'-hydroxy-2',6',8'-trimethyl-1',2',4'a,5',6',7',8',8'a-octahydronaphthalen-1'-yl)penta-2,4-dienoate (compound RS10)

Compound RS10 was synthesized in the same manner as in Synthesis Example 1, except that, in dehydration condensation reaction of compound 2-3, 2-pyridinemethanol was used in place of 5-aminomethyl-1,3-oxazole. The physical property values of compound RS10 are as follows.

RS10

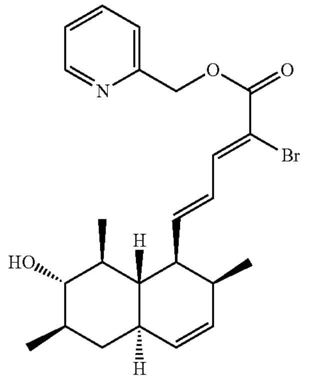

Pyridin-2"-ylmethyl (2Z,4E)-2-bromo-5-((1'S,2'S,4'aR,6'R,7'S,8'S,8'aS)-7'-hydroxy-2',6',8'-trimethyl-1',2',4'a,5',6',7',8',8'a-octahydronaphthalen-1'-yl)penta-2,4-dienoate (compound RS10)

$^1$H NMR (500 MHz, acetone-$d_6$): δ 8.56 (d, J=4.5 Hz, 1H, H-6"), 7.89 (d, J=10.5 Hz, 1H, H-3), 7.82 (ddd, J=8.0, 7.5, 1.5 Hz, 1H, H-4"), 7.49 (d, J=8.0 Hz, 1H, H-3"), 7.32 (dd, J=7.5, 4.5 Hz, 1H, H-5"), 6.70 (dd, J=15.0, 11.0 Hz, 1H, H-4), 6.49 (dd, J=15.0, 10.0 Hz, 1H, H-5), 5.60 (ddd, J=9.0, 4.0, 3.0 Hz, 1H, H-4'), 5.48 (ddd, J=10.0, 2.0, 1.5 Hz, 1H, H-3'), 5.34 (d, J=1.5 Hz, 2H, $CH_2$Ar), 3.49 (d, J=6.5 Hz, 1H, H-7'), 2.67-2.58 (m, 2H, H-8', H-1'), 2.31-2.19 (m, 1H, H-2'), 1.95-1.85 (m, 1H, H-4'a), 1.75 (ddd, J=13.5, 3.5, 3.5 Hz, 1H, H-5'), 1.57-1.40 (m, 1H, H-5'), 1.38-1.25 (m, 1H, H-8'a), 1.09 (d, J=6.0 Hz, 3H, 8'-Me), 1.02 (d, J=7.0 Hz, 3H, 2'-Me), 0.99 (d, J=6.5 Hz, 3H, 6'-Me).

HRMS (ESI): m/z calcd for $C_{24}H_{30}BrNO_3Na$ 482.1301 $[M+Na]^+$; found 482.1318.

Test Example 1

Figure 2:
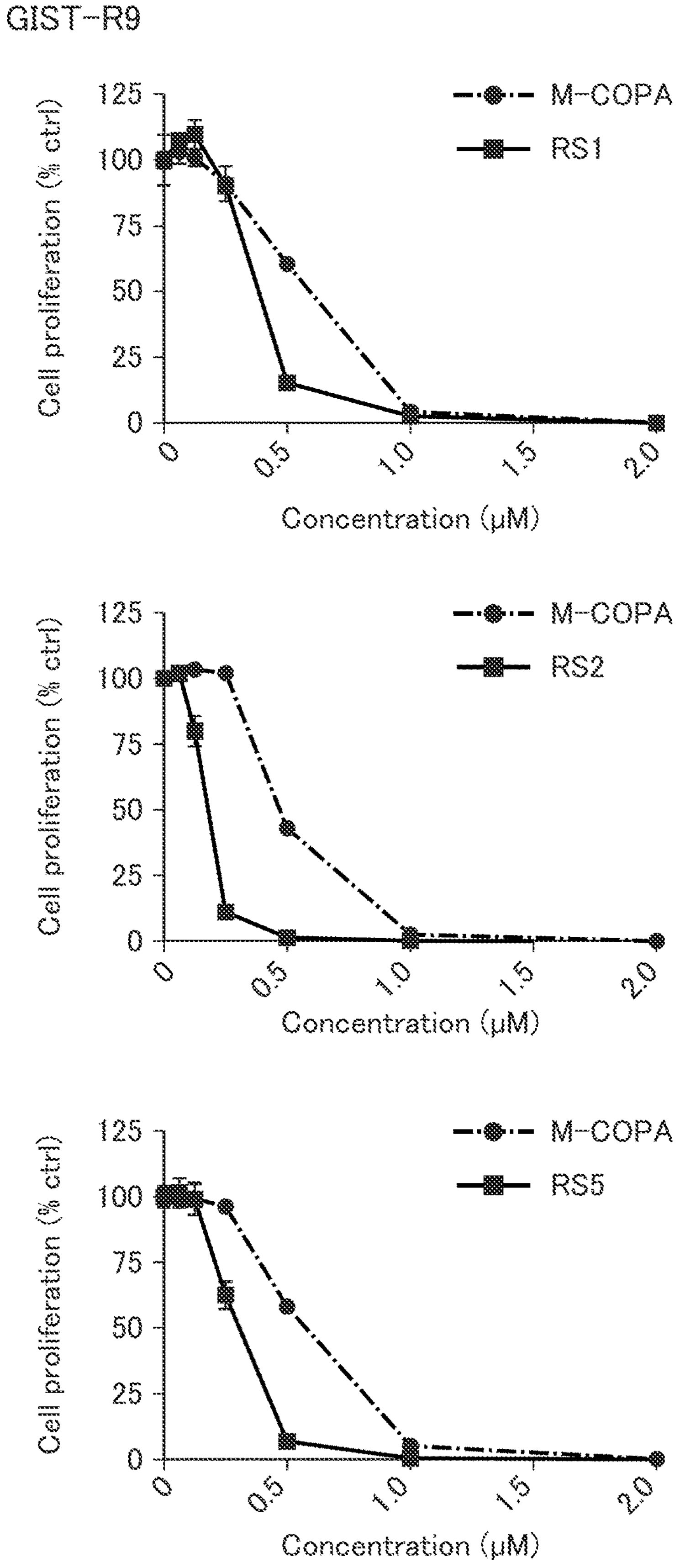
FIG. 2 is graphs showing cell culture curves obtained in culturing GIST-R9 cells in the presence of a compound (RS1, RS2, RS5, or M-COPA) at different concentrations.
Figure 3:
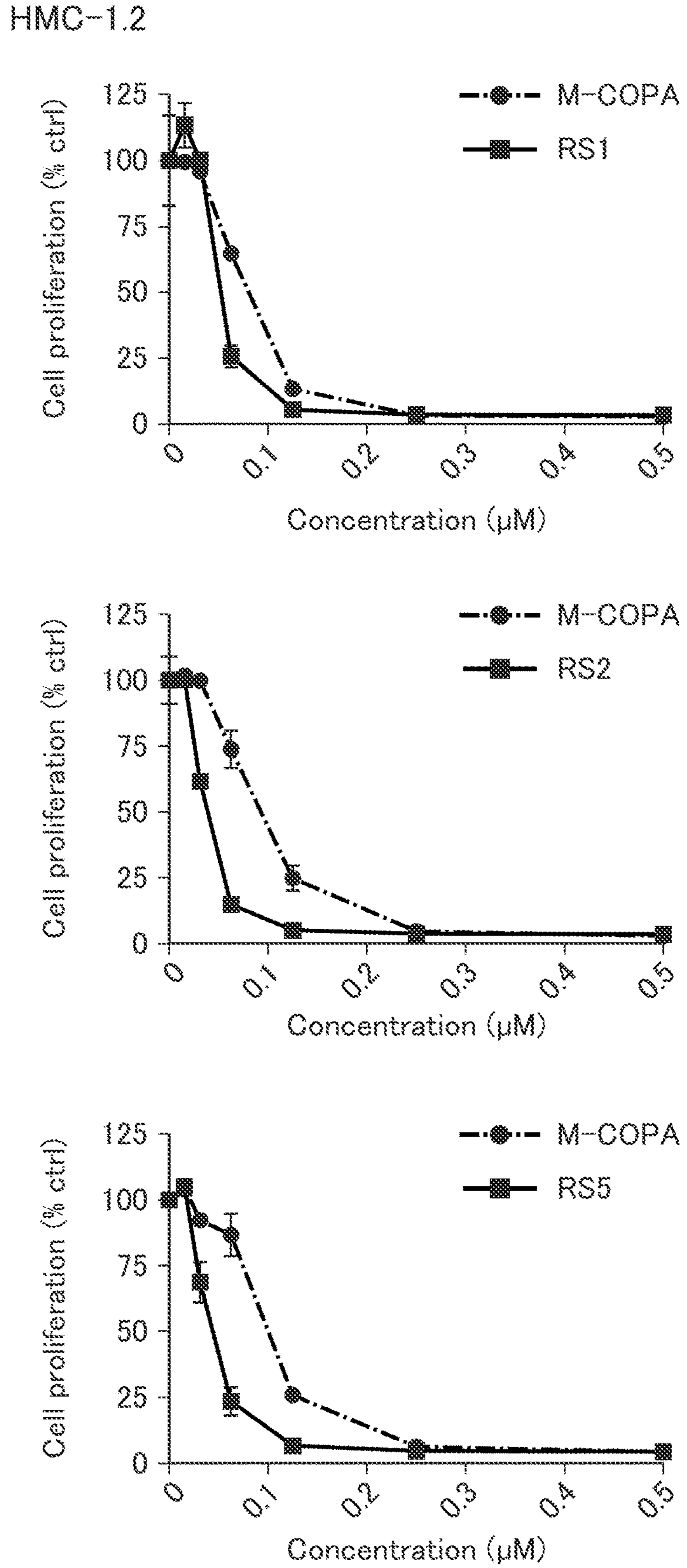
FIG. 3 is graphs showing cell culture curves obtained in culturing HMC-1.2 cells in the presence of a compound (RS1, RS2, RS5, or M-COPA) at different concentrations.

Compounds RS1, RS2, and RS5 obtained in Synthesis Examples 1, 2, and 5, and M-COPA synthesized in the same manner as in Synthesis Example 1 in Patent Document 1 were examined for cell proliferation inhibitory activity against human cultured cancer cells with KIT tyrosine kinase mutation. The human cultured cancer cells used were GIST-T1 cells ($KIT^{\Delta 560-578}$. imatinib-sensitive) and GIST-R9 cells ($KIV^{\Delta 560-578/D820V}$, imatinib-resistant) as gastrointestinal stromal tumor cell lines, and HMC-1.2 cells ($KIT^{V560G/D816V}$, imatinib-resistant) as a mast cell leukemia cell line. The cancer cells of each type were seeded on a 96-well plate and cultured overnight, and cultured for 2 days with addition of serially diluted products of the compounds, and the cell proliferation was then measured by quantifying the ATP production (n=3). FIG. 1 to FIG. 3 show the cell proliferation curves for the GIST-T1 cells, GIST-R9 cells, and HMC-1.2 cells. Table 1 shows $IC_{50}$ values of the compounds.

TABLE 1

| $IC_{50}$ (nM) | M-COPA | RS1 | RS2 | RS5 |
|---|---|---|---|---|
| GIST-T1 | 347 ± 21 | 268 | 128 | 169 |
| GIST-R9 | 528 ± 59 | 363 | 169 | 292 |
| HMC-1.2 | 86 ± 9 | 50 | 37 | 42 |

As shown in FIG. 1 to FIG. 3 and Table 1, compounds RS1, RS2, and RS5 inhibited the cell proliferation of the GIST-T1 cells, GIST-R9 cells, and HMC-1.2 cells in a concentration-dependent manner, and the $IC_{50}$ values of them were lower than that of M-COPA. In particular, as is understood from comparison between compound RS5 and M-COPA, it was demonstrated that substitution of the methyl group in the structure of M-COPA with a bromine atom results in significantly improved anticancer activity.

Test Example 2

Compounds RS1 to RS7 obtained in Synthesis Examples 1 to 7, and M-COPA synthesized in the same manner as in Synthesis Example 1 in Patent Document 1 were examined for cell proliferation inhibitory activity against human cultured cancer cells. The cancer cells used were eight human cancer cell lines (one skin cancer cell line, one ovarian cancer cell line, one prostate cancer cell line, two lung adenocarcinoma cell lines, one colorectal cancer cell line, two breast adenocarcinoma cell lines). The cancer cells of each type were seeded on a 96-well plate and cultured for 2 days, and cultured for 2 days with addition of serially diluted products of the compounds, and the cell proliferation was then measured by colorimetry with a water-soluble tetrazolium salt (WST-8). Thereafter, 50% cell proliferation inhibitory concentrations ($GI_{50}$) were calculated from the cell proliferation curves. Table 2 shows $GI_{50}$ values of the compounds.

TABLE 2

| $GI_{50}$ (μM) | M-COPA | RS1 | RS2 | RS3 | RS4 | RS5 | RS6 | RS7 |
|---|---|---|---|---|---|---|---|---|
| Hs925t (Skin cancer cell line) | 0.05 | 0.001 | 3E−04 | 0.03 | 0.01 | 1E−04 | 0.003 | 0.03 |
| SK-OV3 (Ovarian cancer cell line) | 0.03 | 0.005 | 0.003 | 0.03 | 0.04 | 0.001 | 0.005 | 0.05 |
| DU-145 (Prostate cancer cell line) | 0.1 | 0.04 | 0.01 | 0.2 | 0.3 | 0.01 | 0.05 | 0.3 |
| H1650 (Lung adenocarcinoma cell line) | 0.08 | 0.005 | 0.03 | 0.08 | 0.07 | 0.05 | 0.1 | 0.1 |
| H2228 (Lung adenocarcinoma cell line) | 0.04 | 0.01 | 0.04 | 0.05 | 0.07 | 0.03 | 0.1 | 1 |
| DLD-1 (Colorectal cancer cell line) | 0.03 | 0.003 | 0.001 | 0.03 | 0.04 | 3E−04 | 0.04 | 0.03 |
| MCF-7 (Breast adenocarcinoma cell line) | 0.35 | 0.03 | 0.03 | 0.3 | 0.5 | 0.08 | 0.1 | 1 |
| Hs578t (Breast adenocarcinoma cell line) | 0.04 | 0.003 | 0.03 | 0.003 | 0.03 | 0.03 | 0.03 | 0.01 |

As shown in Table 2, compounds RS1 to RS7 exhibited cell proliferation inhibitory activity significantly superior to that of M-COPA against many of the cancer cell lines.

Test Example 3

Compounds RS8 to RS10 obtained in Synthesis Examples 8 to 10 were examined for cell proliferation inhibitory activity against human cultured cancer cells. The cancer cells used were two human lung adenocarcinoma cell lines and one human lung squamous cell carcinoma cell line. The cancer cells of each type were seeded on a 96-well plate and cultured for 2 days, and cultured for 2 days with addition of serially diluted products of the compounds, and the cell proliferation was then measured by colorimetry with a water-soluble tetrazolium salt (WST-8). Thereafter, 50% cell proliferation inhibitory concentrations ($GI_{50}$) were calculated from the cell proliferation curves. Table 3 shows $GI_{50}$ values of the compounds.

TABLE 3

| $GI_{50}$ (μM) | RS8 | RS9 | RS10 |
|---|---|---|---|
| H1650 (Lung adenocarcinoma cell line) | 0.3 | 0.2 | 0.5 |
| H2228 (Lung adenocarcinoma cell line) | 0.3 | 0.4 | 0.7 |
| H226 (Lung squamous cell carcinoma cell line) | 0.04 | 0.04 | 0.3 |

As shown in Table 3, compounds RS8 to RS10 exhibited superior cell proliferation inhibitory activity against various cancer cell lines, in particular, against the lung squamous cell carcinoma cell line H226.

The invention claimed is:

1. A compound represented by formula (1) below:

(1)

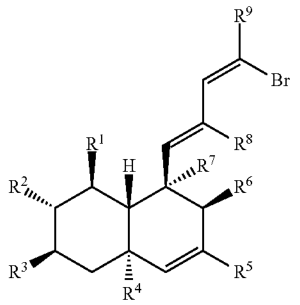

wherein $R^1$ and $R^3$ to $R^8$ each independently represents a hydrogen atom or an alkyl group; $R^2$ represents a hydrogen atom, or a group represented by —$OR^a$ or —$NR^bR^c$; $R^9$ represents a group represented by —$CH_2OR^d$, —$C(O)OR^d$, —$C(O)R^4$, —$CH_2NR^eR^f$, or —$C(O)NR^eR^f$; and $R^a$ to $R^f$ each independently represents a hydrogen atom, an alkyl group, an aryl group optionally having a substituent, a heteroaryl group optionally having a substituent, an arylalkyl group optionally having a substituent, or a heteroarylalkyl group optionally having a substituent.

2. The compound according to claim 1, wherein, in formula (1), $R^1$ and $R^6$ are each independently an alkyl group, $R^2$ is a hydroxy group, $R^4$, $R^5$, $R^7$, and $R^8$ are each a hydrogen atom, $R^9$ is a group represented by —$C(O)OR^d$ or —$C(O)NR^eR^f$, $R^d$ is an arylalkyl group or a heteroarylalkyl group, $R^e$ is a hydrogen atom, and $R^f$ is an arylalkyl group or a heteroarylalkyl group.

3. An intermediate represented by formula (3) below:

(3)

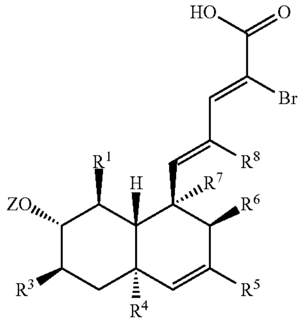

wherein $R^1$ and $R^3$ to $R^8$ each independently represents a hydrogen atom or an alkyl group; and Z represents a protecting group for a hydroxy group.

4. A method for producing a compound represented by formula (1) below:

(1)

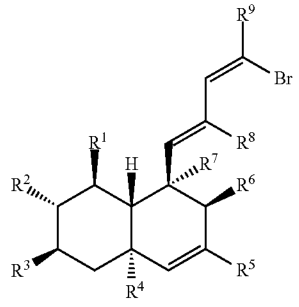

wherein $R^1$ and $R^3$ to $R^8$ each independently represents a hydrogen atom or an alkyl group; $R^2$ represents a hydrogen atom, or a group represented by $—OR^a$ or $—NR^bR^c$; $R^9$ represents a group represented by $—CH_2OR^d$, $—C(O)OR^d$, $—C(O)R^d$, $—CH_2NR^eR^f$, or $—C(O)NR^eR^f$; and $R^a$ to $R^f$ each independently represents a hydrogen atom, an alkyl group, an aryl group optionally having a substituent, a heteroaryl group optionally having a substituent, an arylalkyl group optionally having a substituent, or a heteroarylalkyl group optionally having a substituent, the method comprising converting a compound represented by formula (3) below into a compound represented by formula (1):

(3)

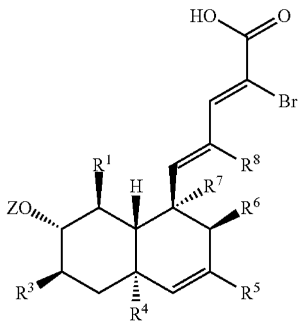

wherein $R^1$ and $R^3$ to $R^8$ are as described above; and Z represents a protecting group for a hydroxy group.

5. The method according to claim 4, wherein the compound represented by formula (3) is produced by subjecting a compound represented by formula (6) below and a compound represented by formula (5) below to a Horner-Wadsworth-Emmons reaction followed by hydrolysis:

(6)

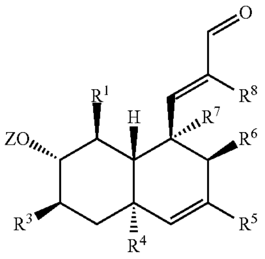

wherein $R^1$, and $R^3$ to $R^8$ each independently represents a hydrogen atom or an alkyl group; $R^2$ represents a hydrogen atom, or a group represented by $—OR^a$ or $—NR^bR^c$; $R^9$ represents a group represented by $—CH_2OR^d$, $—C(O)OR^d$, $—C(O)R^d—CH_2NR^eR^f$, or $—C(O)NR^eR^f$; and $R^a$ to $R^f$ each independently represents a hydrogen atom, an alkyl group, an aryl group optionally having a substituent, a heteroaryl group optionally having a substituent, an arylalkyl group optionally having a substituent, or a heteroarylalkyl group optionally having a substituent, and Z represents a protecting group for a hydroxy group, (5)

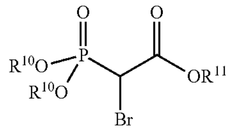

and wherein $R^{10}$ and $R^{11}$ each independently represents an alkyl group.

6. The production method according to claim 5, wherein the compound represented by formula (6) is produced by cyclizing a compound represented by formula (7) below through an intramolecular Diels-Alder reaction:

(7)

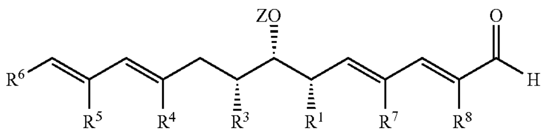

wherein $R^1$, $R^3$ to $R^8$ each independently represents a hydrogen atom or an alkyl group; $R^2$ represents a hydrogen atom, or a group represented by $—OR^a$ or $—NR^bR^c$; $R^9$ represents a group represented by $—CH_2OR^d$, $—C(O)OR^d$, $—C(O)R^d$, $—CH_2NR^eR^f$, or $—C(O)NR^eR^f$; and $R^a$ to $R^f$ each independently represents a hydrogen atom, an alkyl group, an aryl group optionally having a substituent, a heteroaryl group optionally having a substituent, an arylalkyl group optionally having a substituent, or a heteroarylalkyl group optionally having a substituent, and Z represents a protecting group for a hydroxy group.

7. A pharmaceutical composition comprising the compound according to claim 1 and a pharmaceutically acceptable carrier.

* * * * *